(12) United States Patent
Karoum et al.

(10) Patent No.: US 11,732,580 B2
(45) Date of Patent: Aug. 22, 2023

(54) NMR SENSOR FOR MONITORING MULTI-PHASE FLUID SETTLING

(71) Applicant: Schlumberger Technology Corporation, Sugar Land, TX (US)

(72) Inventors: Reda Karoum, Houston, TX (US); Yiqiao Tang, Belmont, MA (US); Shin Utsuzawa, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 71 days.

(21) Appl. No.: 17/114,575

(22) Filed: Dec. 8, 2020

(65) Prior Publication Data
US 2022/0178253 A1    Jun. 9, 2022

(51) Int. Cl.
*E21B 49/08*      (2006.01)
*G01N 33/28*      (2006.01)
*G01N 24/08*      (2006.01)

(52) U.S. Cl.
CPC ........ *E21B 49/0875* (2020.05); *E21B 49/086* (2013.01); *G01N 24/08* (2013.01); *G01N 33/2823* (2013.01)

(58) Field of Classification Search
CPC .... E21B 49/0875; E21B 49/086; E21B 21/01; G01N 24/08; G01N 33/2823; G01N 24/081; G01R 33/30; G01R 33/3808; G01R 33/383; G01R 33/448
See application file for complete search history.

(56) References Cited

U.S. PATENT DOCUMENTS

| | | | |
|---|---|---|---|
| 9,194,972 B2 * | 11/2015 | Van Der Zwaag | G01V 3/32 |
| 9,777,542 B2 | 10/2017 | Stock et al. | |
| 11,047,815 B2 | 6/2021 | Reiderman | |
| 2020/0301039 A1 | 9/2020 | Tang et al. | |
| 2022/0050223 A1 | 2/2022 | Tang et al. | |

FOREIGN PATENT DOCUMENTS

| | | |
|---|---|---|
| WO | 2019060098 A1 | 3/2019 |
| WO | 2019222300 A1 | 11/2019 |

OTHER PUBLICATIONS

Utsuzawa et al., "Unilateral NMR with a barrel magnet." Journal of Magnetic Resonance 282, 2017, pp. 104-113.
Rismanto et al., "Explorative Study of NMR Drilling Fluids Measurement", Annual Transactions of the Nordic Theology Society, vol. 15, 2007, 7 pages.
Windt, et al., "A portable Halbach magnet that can be opened and closed without force: The NMR-CUFF." Journal of Magnetic Resonance 208.1 (2011): pp. 27-33.

* cited by examiner

*Primary Examiner* — Farhana A Hoque
(74) *Attorney, Agent, or Firm* — Jeffrey D. Frantz

(57) ABSTRACT

An NMR sensor is configured to make NMR measurements of a fluid and includes a housing defining a chamber. A nonmagnetic cap is deployed in the chamber and divides the chamber into first and second regions. The cap is sized and shaped to define a fluid collector in the first region. A magnet assembly is deployed in the second region and is configured to generate a static magnetic field in the fluid collector. A radio frequency (RF) coil is interposed between the magnet assembly and the cap and is configured to generate an RF magnetic field in the fluid collector. Methods include using the sensor to make NMR measurements of multi-phase fluids such as drilling fluid.

29 Claims, 10 Drawing Sheets
(2 of 10 Drawing Sheet(s) Filed in Color)

time since thermal exposure, hours

NMR SENSOR FOR MONITORING MULTI-PHASE FLUID SETTLING

CROSS REFERENCE TO RELATED APPLICATIONS

None.

FIELD OF THE INVENTION

Disclosed embodiments relate generally to a nuclear magnetic resonance (NMR) sensor and NMR methods for monitoring fluid settling and more particularly to an NMR sensor and methods for monitoring fluids, such as drilling fluids used in subterranean wellbore operations.

BACKGROUND INFORMATION

The use of nuclear magnetic resonance (NMR) measurements in oilfield applications is well known, for example, to evaluate drilling fluid or formation core samples as well as to make downhole measurements in the wellbore. Such techniques may be utilized to determine various characteristics of porous subterranean formations and to assist in the determination of, for example, the presence, absence, location, mobility, and producibility of hydrocarbons in the formation.

NMR measurements are made by applying a strong, polarizing, static magnetic field (the longitudinal magnetic field) to a sample (such as a drilling fluid or formation core sample). This field causes the proton spins to align in a direction parallel to the applied field. A series of radio frequency (RF) pulses are then transmitted into the sample to rotate the magnetization into the transverse plane. Carr-Purcell-Meiboom-Gill (CPMG) pulse sequences are commonly employed in downhole and oilfield applications. The RF pulses generate a series of spin echoes that bear information about various properties of the interrogated sample such as volumes of liquids, their relaxation times, and diffusion properties.

Time constants $T_1$ and $T_2$ are commonly evaluated in NMR measurements. The spin-lattice relaxation time $T_1$ (also referred to as the longitudinal polarization time T1) is the time constant for the longitudinal magnetization to return to its thermal equilibrium value in the static magnetic field. The spin-spin relaxation time $T_2$ (also referred to as the transverse polarization time T2) is the time constant for the transverse magnetization to return to its thermal equilibrium value of zero. Diffusion coefficients of the liquids in the formation are also known to influence the relaxation processes. Distributions of these relaxation times may be inferred from the amplitudes of the measured spin echoes by $T_1$, $T_2$, and diffusion inversions. Such inversions (generally Laplacian inversions) may provide both one-dimensional distributions of any of those quantities and/or multi-dimensional joint distributions of any subset of them.

As is known to those of ordinary skill, drilling fluids are highly complex multi-phase fluids. Drilling fluids are subject to temperatures and/or pressures that can significantly exceed ambient temperature and pressure conditions and commonly undergo phase separation or other molecular dynamics during static aging at those conditions. Understanding and/or monitoring the aging process is important to predicting drilling fluid performance in high temperature and/or elevated (non-ambient) pressure downhole conditions. While various methods exist to study fluid settling, there are numerous difficulties owing to the harsh downhole conditions as well as the complexity of the fluids. There is a need in the art for improved methods for monitoring and studying drilling fluids, particularly improved NMR methods and improved NMR sensors.

SUMMARY

An NMR sensor is disclosed. The sensor is configured to make NMR measurements of a fluid and includes a housing defining a chamber. A nonmagnetic cap is deployed in the chamber and divides the chamber into first and second regions. The cap is sized and shaped to define a fluid collector in the first region. A magnet assembly is deployed in the second region and is configured to generate a static magnetic field in the fluid collector. A radio frequency (RF) coil is interposed between the magnet assembly and the cap and is configured to generate an RF magnetic field in the fluid collector.

A method for evaluating drilling fluid is further disclosed. The method includes deploying at least one NMR sensor in fluid communication with drilling fluid at a surface location in a drilling rig. The NMR sensor includes (i) a sensor housing defining a chamber, the chamber in fluid communication with the drilling fluid, (ii) a magnet assembly deployed in the chamber and configured to generate a static magnetic field in at least a portion of the chamber, (iii) a radio frequency (RF) coil deployed in the chamber and configured to generate an RF magnetic field in at least the portion of the chamber, and (iv) a nonmagnetic cap deployed in the chamber and configured to provide a fluid tight seal between the drilling fluid and the magnet assembly and the RF coil. The NMR sensor is used to make a plurality of NMR measurements of the drilling fluid at a corresponding plurality of times during operation of the drilling rig. The NMR measurements are then processed to determine at least one property of the drilling fluid and/or to monitor changes in the drilling fluid over the plurality of times.

Another method for evaluating a fluid is further disclosed. The method includes obtaining a sample of the fluid and using an NMR measurement sensor to make a plurality of NMR measurements of the sample at a corresponding plurality of times while the sample ages. The NMR sensor includes (i) a housing defining a chamber, (ii) a nonmagnetic cap deployed in the chamber and dividing the chamber into first and second regions, the cap sized and shaped to define a fluid collector in the first region, (iii) a magnet assembly deployed in the second region, the magnet assembly configured to generate a static magnetic field in the fluid collector, and (iv) a radio frequency (RF) coil interposed between the magnet assembly and the cap, the coil configured to generate an RF magnetic field in the fluid collector. The NMR measurements are then processed to determine at least one property of the fluid and/or to monitor changes in the fluid over the plurality of times.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the disclosed subject matter, and advantages thereof, reference is now made to the following descriptions taken in conjunction with the accompanying drawings, in which:

FIG. 8A plots the magnetic field in units of Gauss versus distance along the sensor axis.

FIG. 8B plots the magnetic field in units of Gauss versus distance along a lateral or radial direction perpendicular to the axis (at an axial distance of 6 mm).

FIG. 9A plots the magnetic field in units of Gauss versus distance along the sensor axis. FIG. 9B plots the magnetic field in units of Gauss versus distance along a lateral or radial direction perpendicular to the axis (at an axial distance of 6 mm).

DETAILED DESCRIPTION

As described above in the Background section of this disclosure, NMR is a measurement technology commonly used in oilfield applications to evaluate porous media and complex fluids. Oilfield NMR generally evaluates hydrogen spins in fluids, which when subject to an external static magnetic field embody two distinctive energy levels with a small gap $\Delta E$. Upon applying an AC magnetic field at frequency $f=\Delta E/h$ (where h is the Planck's constant) for a definite time, a spin resonance is created and as a result an NMR signal is excited. The resonance condition may be further controlled through a set of AC and/or DC magnetic-field pulses in the time domain. For a specific time sequence of AC/DC pulses, the evolution of NMR signal relates to certain fluid characteristics.

Oilfield NMR measurements are commonly acquired using radio-frequency (RF) AC pulse sequences. One common pulse sequence used to measure the $T_2$ relaxation time distribution is referred to as the Carr-Purcell-Meiboom-Gill (CPMG) sequence. A CPMG sequence includes an initial idle time or wait time to allow the nuclei in fluids to come to equilibrium with the $B_0$ magnetic field, e.g., induced by one or more permanent magnets in the tool. A series of RF pulses is then applied using one or more RF coils. Echoes are received by the coil(s) between adjacent pulses. The echo amplitude decays with time during the sequence. A $T_2$ distribution may be determined by fitting the echo amplitudes to a multi-exponential model as is known to those of ordinary skill in the art.

Figure 1:
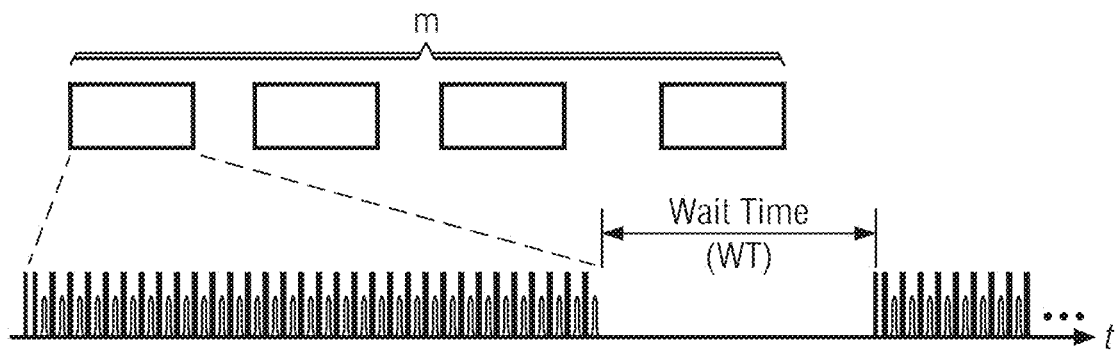
FIG. 1 depicts an example CMPG pulse sequence.

More advanced measurements make use of a stack (or set) of CPMG pulse sequences separated by corresponding wait times (WTs) to measure both $T_1$ and $T_2$ distributions, for example, as depicted on FIG. 1. This set of CPMG sequences is commonly referred to as a "saturation-recovery" CPMG sequence and can be used to generate NMR signals (echoes) as expressed mathematically below:

$$S(WT, n, TE) = \int dT_1 dT_2 f(T_1, T_2) K(WT, n, TE, T_1, T_2)$$

where $S(WT, t_{echo})$ represents the NMR signal, $$K(WT, n, TE, T_1, T_2) = M_0 \left(1 - \exp\left(-\frac{WT}{T_1}\right)\right) \exp\left(-n\frac{TE}{T_2}\right)$$

and where $M_0$ is proportional to porosity. The kernel function $K(\ldots)$ describes spin dynamics of excited proton signals as a function of pulsing parameters, WT, n, and TE, as well as intrinsic formation properties $T_1$ and $T_2$. A joint probability distribution $f(T_1, T_2)$ obtained via such measurements presents distinctive signatures of complex fluids (e.g., in two dimensional $T_1$ versus $T_2$ plots as described in more detail below).

Oilfield NMR investigates fluid dynamics at a molecular level, and therefore tends to be intrinsically sensitive to properties of fluid molecules themselves and their surroundings. At an operating frequency of a few to tens of MHz the NMR method is essentially unaffected by the presence of emulsions since the RF wavelength is greater than the size of dispersed droplets under study. The intrinsic physics makes NMR a suitable tool to investigate complex fluids of multiple phases.

As noted above in the Background Section, drilling fluids tend to be highly complex multi-phase fluids that are commonly subject to non-ambient (e.g., elevated) temperature and/or pressure conditions. Fluid settling and phase separation is a ubiquitous phenomenon and difficulty in oilfield operations. There is a need in the art for improved NMR sensors and methods for in-situ monitoring and study of drilling aging and settling processes.

Disclosed NMR sensor embodiments may advantageously enable fluid settling and phase separation to be monitored and studied at both ambient conditions and operational conditions (e.g., elevated temperature and/or elevated pressure). The sensor embodiments may advantageously include a fluid collector that accelerates or promotes fluid settling and separation and therefore enables more timely evaluation of the fluid aging/settling processes.

Moreover, certain disclosed NMR sensor embodiments may be deployed at the rig surface to monitor fluid changes in real time and in-situ during a drilling or completion operation. The sensors may be advantageously deployed in fluid communication with the drilling fluid in operation, for example, in a mud pit, a standpipe, or a fluid return passageway. Disclosed NMR sensor embodiments may also be used in a laboratory environment to study fluid aging, for example, settling and separation, to determine various fluid properties such as an NMR stability index (a quantitative index indicative of a stability (or instability) of a multi-phase fluid sample), various settling and separation rates, and various NMR fluid parameters such as $T_1$ and $T_2$ relaxation times.

Figure 2:
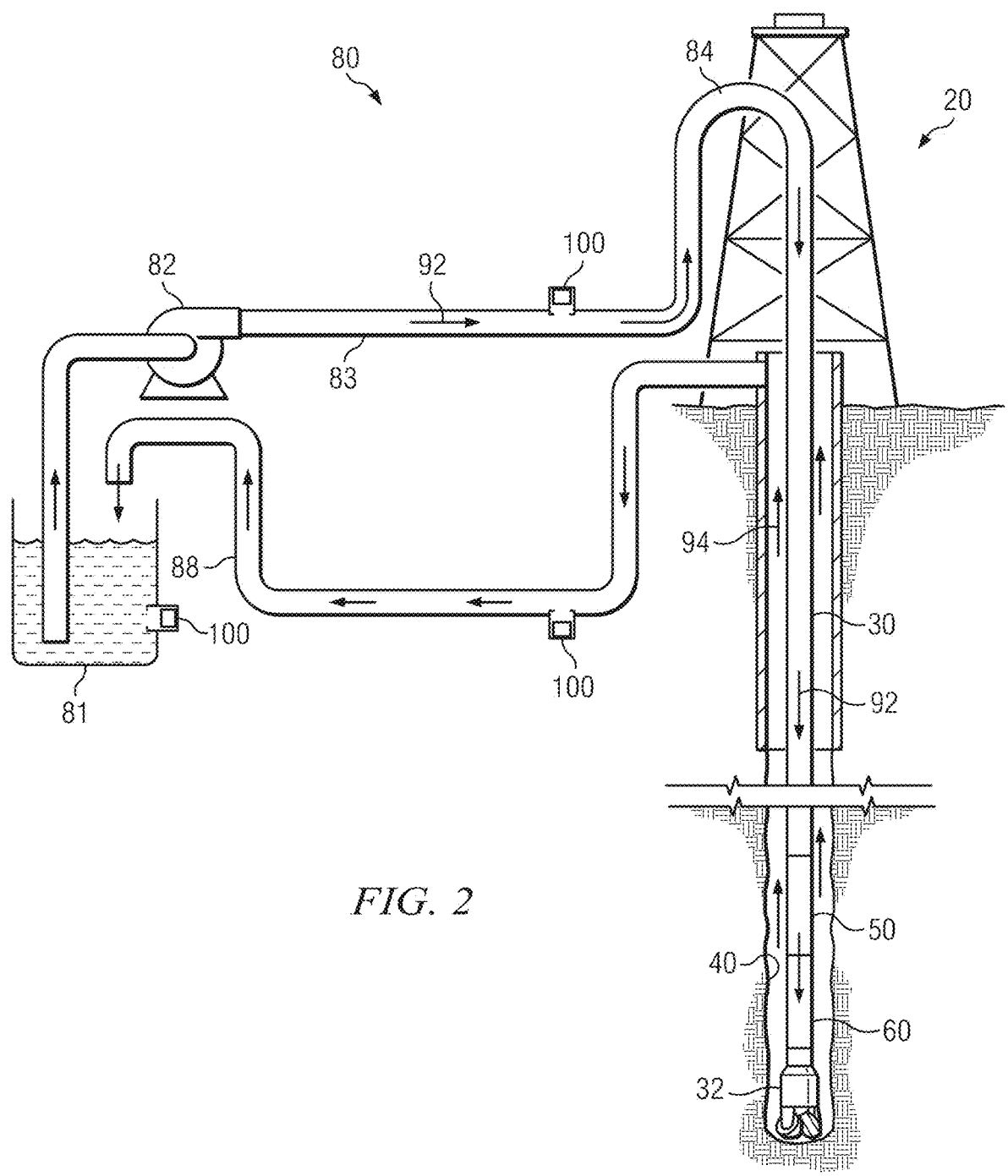
FIG. 2 depicts an example drilling rig on which example sensor embodiments and method embodiments may be utilized.

FIG. 2 depicts an example drilling rig 20 on which example NMR sensor embodiments and method embodiments may be utilized. The drilling rig may be positioned over a subterranean oil or gas formation (not shown). The rig may include, for example, a derrick and a hoisting apparatus (also not shown) for raising and lowering a drill string 30, which, as shown, extends into wellbore 40 and includes, for example, a drill bit 32 and other downhole tools 50 (such as a steering tool, a logging while drilling tool, a measurement while drilling tool, and the like).

Drilling rig 20 includes a surface system 80 for controlling the flow of drilling fluid used on the rig (e.g., used in drilling the wellbore 40). In the example embodiment depicted, drilling fluid is pumped downhole (as depicted at 92) via a conventional mud pump 82. The drilling fluid may be pumped, for example, through a standpipe 83 and mud hose 84 en route to the drill string 30. The drilling fluid typically emerges from the drill string 30 at or near the drill bit 32 and creates an upward flow 94 of mud through the wellbore annulus (the annular space between the drill string and the wellbore wall). The drilling fluid then flows through a return conduit 88 to mud pit 81.

As described above, the disclosed sensor and method embodiments may be advantageously utilized to evaluate drilling fluid in use in a drilling rig (such as rig 20). With continued reference to FIG. 2, surface system 80 may include one or more NMR sensors 100 (shown schematically) configured for making NMR measurements of the drilling fluid in the system 80. For example, NMR sensors 100 may be deployed in the mud pit 81, the standpipe 92, and/or the return passageway 88. As described in more detail below, the NMR sensors 100 may be advantageously configured to be in fluid communication (direct fluid contact) with the drilling fluid in the mud pit 81, the standpipe 92, and/or the return passageway 88 (e.g., such that the fluid enters into an interior region of the sensor).

Figure 3A:
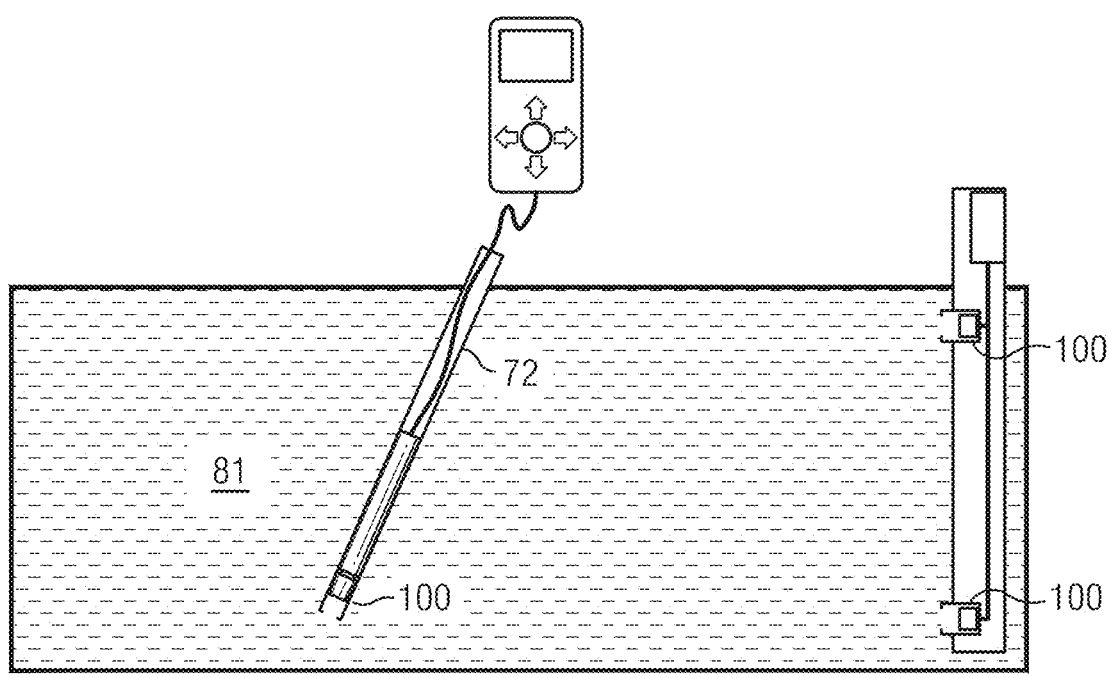
FIGS. 3A and 3B depict example NMR sensor deployments in a mud pit (3A) and a conduit (3B).
Figure 3B:
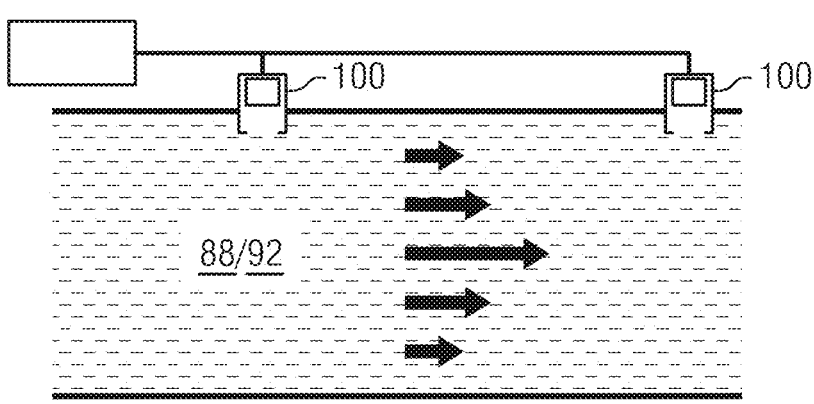

FIGS. 3A and 3B (collectively FIG. 3) depict example NMR sensor 100 deployments (e.g., in surface system 80). In FIG. 3A an example mud pit 81 includes NMR sensors 100 deployed therein. For example, the NMR sensors 100 may be deployed near the top and bottom of a sidewall of the mud pit 81. Likewise, the NMR sensors may be deployed along the bottom surface of the mud pit or may be deployed at the end of a wand 72 (or stick) that may be hand held or otherwise suspended in the drilling fluid as depicted. FIG. 3B depicts an example conduit (e.g., standpipe 92 or return passageway 88) including an NMR sensor 100 deployed in the sidewall of the conduit and in fluid communication with the drilling fluid therein. As further depicted in FIGS. 3A and 3B, the NMR sensors 100 may be in electronic communication with an electronic controller or computer configured to process and/or store NMR measurements.

Figure 4A:
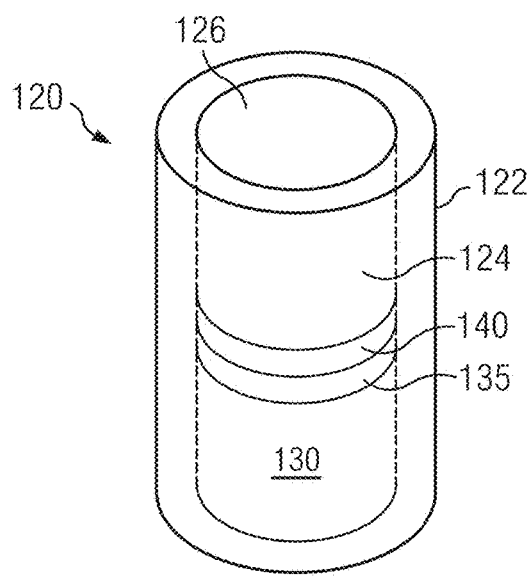
FIGS. 4A and 4B depict example NMR sensors for use in the deployments shown on FIGS. 3A and 3B.
Figure 4B:
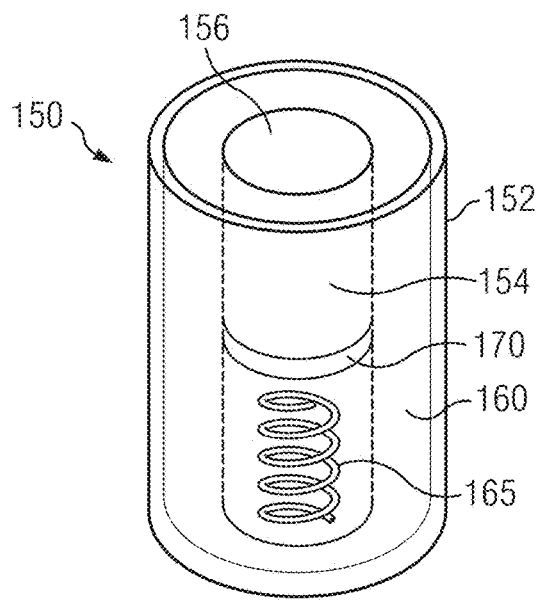

It will be understood that the NMR sensors may be advantageously deployed in fluid communication with the drilling fluid such that NMR measurements may be made during the operation of the drilling rig. FIGS. 4A and 4B depict example NMR sensors that may be suitable for use in surface system 80 (e.g., as depicted on FIGS. 3A and/or 3B).

FIG. 4A depicts NMR sensor 120 that may be deployed in surface system 80. Sensor 120 includes a sensor housing 122 defining an internal chamber 124. Chamber 124 is open ended (as depicted at 126) such that the chamber 124 is in fluid communication with drilling fluid external to the housing 122 (e.g., in the mud pit, the standpipe, and/or the return passageway). A magnet assembly 130 is deployed in the chamber and is configured to generate a static magnetic field in at least a portion of the chamber (e.g., in a sensitive region). A radio frequency (RF) coil 135 is also deployed in the coil and is configured to generate an RF magnetic field in at least a portion of the chamber (e.g., in a sensitive region). Sensor 120 further includes a nonmagnetic cap 140 deployed between the magnet assembly 130 and RF coil 135 on one end of the chamber 124 and open end 126 on the other end of the chamber. The cap 140 is configured to provide a fluid tight seal between the drilling fluid in chamber 124 and the magnet assembly 130 and the RF coil 135. As described in more detail below, the cap 140 may optionally include a fluid collector (not shown on FIG. 4A) shaped to promote accelerated settling of solid components in the drilling fluid.

FIG. 4B depicts NMR sensor 150 that may be deployed in surface system 80. Sensor 150 is similar to sensor 120 in that it includes a sensor housing 152 defining an internal chamber 154 that is open ended (as depicted at 156). Sensor 150 includes a ring (or tubular) shaped magnet assembly 160 that is configured to generate a static magnetic field in a radial direction in the bore. An RF coil 165 may be deployed such that it produces an axially directed RF magnetic field in an inner region of the ring (or tube) (e.g., in a sensitive region). Sensor 150 further includes a nonmagnetic cap 170 deployed between the RF coil 165 on one end of the chamber 154 and open end 156 on the other end of the chamber. The cap 170 is configured to provide a fluid tight seal between the drilling fluid in chamber 154 and the RF coil 165 in the other end of the chamber.

Figure 5:
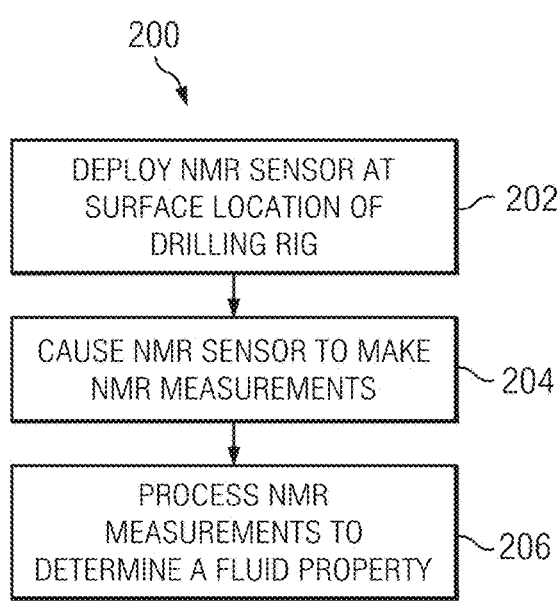
FIG. 5 depicts a flow chart of one disclosed method embodiment for evaluating drilling fluid in a drilling rig.

FIG. 5 depicts a flow chart of one disclosed method embodiment 200 for evaluating drilling fluid in a drilling rig. The method includes deploying one or more NMR sensors at a surface location in the rig at 202. The NMR sensor(s) is/are deployed in fluid communication with the drilling fluid, for example, in a mud pit, a standpipe, and/or a return passageway (e.g., as described above with respect to FIGS. 2 and 3). As described above with respect to FIGS. 4A and 4B, the sensor includes a sensor housing defining a chamber, a magnet assembly configured to generate a static magnetic field (the $B_0$ field) in a region of the chamber, an RF coil configured to generate an RF magnetic field (the $B_1$ field) in the region of the chamber, and a nonmagnetic cap or shield deployed in the chamber and configured to provide a fluid tight seal between the drilling fluid at least one of the magnet assembly and the RF coil.

With continued reference to FIG. 5, method 200 further includes causing the NMR sensor to make a plurality of NMR measurements of the drilling fluid at 204 at a corresponding plurality of times during operation of the drilling rig. The NMR measurements may be made, for example, as described above via applying a CPMG pulse sequence and measuring corresponding pulse echoes. The measurements may be made at any suitable times or substantially any suitable time interval, for example, at 1 hour, 2 hour, 4 hour, 12 hour, or 1 day intervals. The disclosed embodiments are, of course, not limited in this regard.

The NMR measurements may be processed at 206 to determine at least one property of the drilling fluid and/or to monitor changes in the drilling fluid over the measurement time interval (i.e., over the plurality of times). The processing in 206 may include, for example, inverting each of the plurality of NMR measurements to obtain a corresponding plurality of $T_1$ versus $T_2$ plots (referred to herein as T1T2 plots) and evaluating the T1T2 plots to determine the property of the drilling fluid and/or to monitor changes in the drilling fluid with time. The drilling fluid property may include substantially any fluid property, for example, including an NMR stability index, a $T_1$ distribution, a $T_2$ distribution, a diffusion coefficient, a solids concentration (percent solids), and/or an oil/water fraction.

Figure 6:
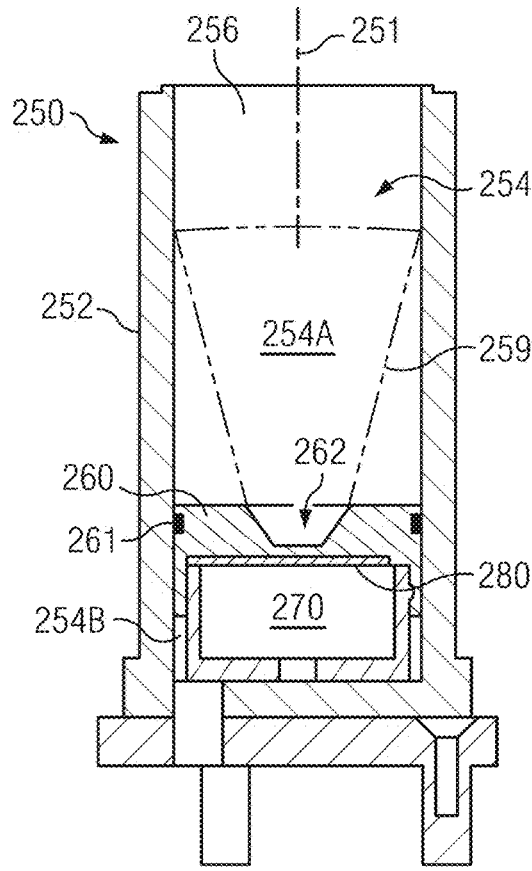
FIG. 6 depicts another NMR sensor embodiment configured for use in making NMR measurements of aging and/or sagging of multi-phase fluids such as drilling fluids.

Turning now to FIG. 6, another NMR sensor embodiment 250 is depicted. Sensor 250 is configured for use in making NMR measurements of multi-phase fluids such as drilling fluids and may be used in surface system 80, for example as described above with respect to sensors 120 or 150, or in a laboratory NMR instrument. Sensor 250 includes a sensor housing 252 defining an inner chamber 254. In the depicted embodiment, the housing 252 includes an open end 256 providing for fluid communication between fluid in the chamber 254 and external to the housing 252. While not depicted, it will be understood that housing 252 may optionally further include a top cap for sealing the chamber 254 after filling with the fluid. Sealing the chamber may be advantageous in making aging measurements of the fluid at non-ambient conditions (e.g., elevated temperature and/or pressure).

A nonmagnetic cap 260 (e.g., a cap fabricated from a nonmagnetic and nonconductive material) is deployed in the chamber 254 and divides the chamber into first and second regions 254A and 254B. In the depicted sensor embodiment, the cap is configured to sealingly engage an inner surface of the housing 252 (e.g., via O-rings 261) and isolate the second region 254B of the chamber 254 from the first region 254A.

A magnet assembly 270 is deployed in the second region. The magnet assembly is configured to generate a static magnetic field (the $B_0$ field) in a fluid collector (e.g., as described in more detail below). An RF coil 280 may be interposed between the magnet assembly 270 and the cap 260. The RF coil 280 is configured to generate an RF magnetic field (the $B_1$ field) in the fluid collector. In the depicted embodiment the magnet assembly 270 and the RF coil are configured to generate approximately uniform $B_0$ and $B_1$ fields in the fluid collector and thereby define a zone of maximum NMR sensitivity in the fluid collector 262 (e.g., as described in more detail below with respect to FIGS. 8 and 9).

With continued reference to FIG. 6, the cap 260 may be sized and shaped to define a fluid collector 262 in the first region 254A. The fluid collector 262 may be advantageously shaped to accelerate (or exaggerate) the effect of settling of solid components in the fluid thereby advantageously reducing the time required to study sagging of the fluid. By accelerate (or exaggerate) it is meant that the shape of the fluid collector 262 causes the concentration of solids to increase faster than it otherwise would have during settling (e.g., in a uniformly shaped chamber).

In the depicted embodiment, the fluid collector is shaped such that a cross sectional area or a lateral dimension (in a plane orthogonal to longitudinal axis 251) is larger distal from the RF coil 280 and smaller proximate to the RF coil 280. In other words, the cross sectional area or lateral dimension of the fluid collector away from (distal to) the RF coil is greater than the cross sectional area or lateral dimension of the fluid collector near (proximate) to the RF coil. In the depicted embodiment, the lateral dimension of the fluid collector 262 increases linearly with increasing distance (along axis 251) from the RF coil 280. The cross sectional area or lateral dimension may alternatively increase monotonically, stepwise, or according to substantially any other mathematical function. Moreover, in certain embodiments, the fluid collector may be described as being conical, pyramidal, or a conical or pyramidal frustum.

With further reference to FIG. 6, sensor 250 may further optionally include a funnel 259 deployed in the first region 254A of the chamber 254 to promote collection of solid sediments in the fluid collector 262. It will be understood that the use of a funnel is entirely optional and may be intended to further accelerate settling of solids in the fluid.

Figure 7A:
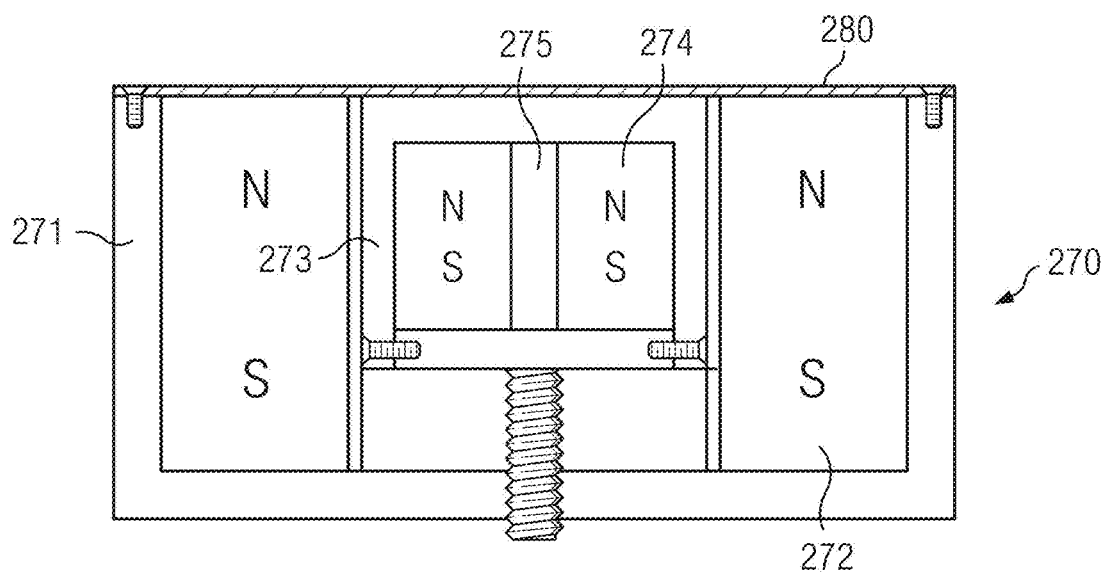
FIG. 7A depicts a cross sectional view of one example magnetic assembly and RF coil configuration suitable for use in the sensor embodiment shown on FIG. 6.

FIG. 7A depicts a cross sectional view of one example embodiment of magnetic assembly 270 and RF coil 280. In the depicted embodiment, magnetic assembly 270 includes a first set (plurality) of inner ring-shaped permanent magnets 274 stacked concentrically with one another and deployed concentrically in a second set (plurality) of outer ring-shaped permanent magnets 272 stacked concentrically with one another. The outer set of magnets is deployed in a nonmagnetic housing 271 (e.g., an aluminum or aluminum alloy housing). The inner set of magnets 274 is deployed in an inner nonmagnetic and nonconductive housing 273, such as a polyether ether ketone (PEEK) housing, which is deployed coaxially with and in the outer set of magnets 272. The inner and outer sets of permanent magnets may include substantially any number of stacked ring-shaped magnets (e.g., 3, 4, 5, or more) and do not necessarily include the same number of magnets. In the depicted embodiment, the interior space 275 may be empty (void). FIG. 7A further depicts the RF coil 280 deployed on one axial end (face) of the magnet assembly 270.

In one particular non-limiting embodiment a magnet assembly was constructed such that the outer magnet stack included four substantially identical ring magnets (each having a 51 mm OD, a 25 mm ID, and a 6.4 mm thickness). The inner magnet stack also included four substantially identical ring magnets (each having a 19 mm OD, a 3.2 mm ID, and a 3.2 mm thickness).

Figure 7B:
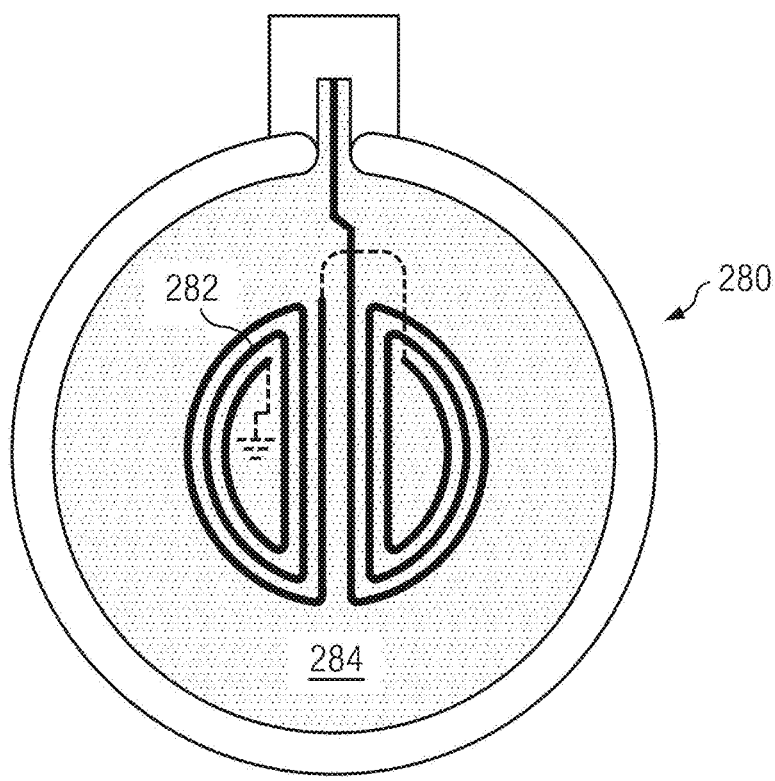
FIG. 7B depicts a side view of one example RF coil configuration suitable for use in the sensor embodiment shown on FIG. 6.

FIG. 7B depicts the side of the RF coil 280 facing the first region 254A of the chamber 254 (i.e., facing the fluid when in service). In the depicted embodiment, the RF coil 280 includes a double-D shaped coil 282 deployed in a three-layer printed circuit board (PCB) 284. In this particular non limiting embodiment, the coil 284 may be implemented on a three-layer PCB with the main windings (three turns on each of the D-halves) on the first layer, a link between two D-halves on the second layer, and the ground plane on the third layer. In one example implementation the inductance was 280 nH and the resistance was 280 mΩ at an operating frequency of 6.8 MHz (hence Q=43). The probe was tuned and 50Ω matched with high-Q mica capacitors.

Figure 8A:
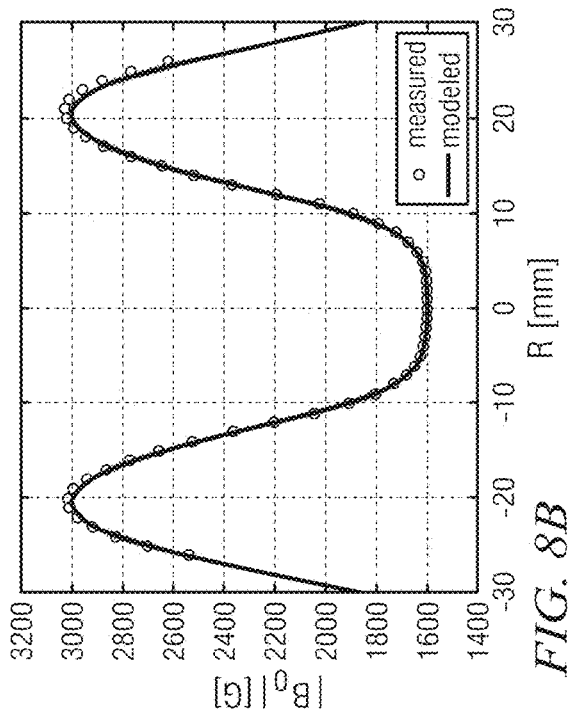
FIGS. 8A and 8B (collectively FIG. 8) depict plots of modelled and measured $B_0$ magnetic fields generated by one example magnetic assembly described with respect to FIG. 7A.
Figure 8B:
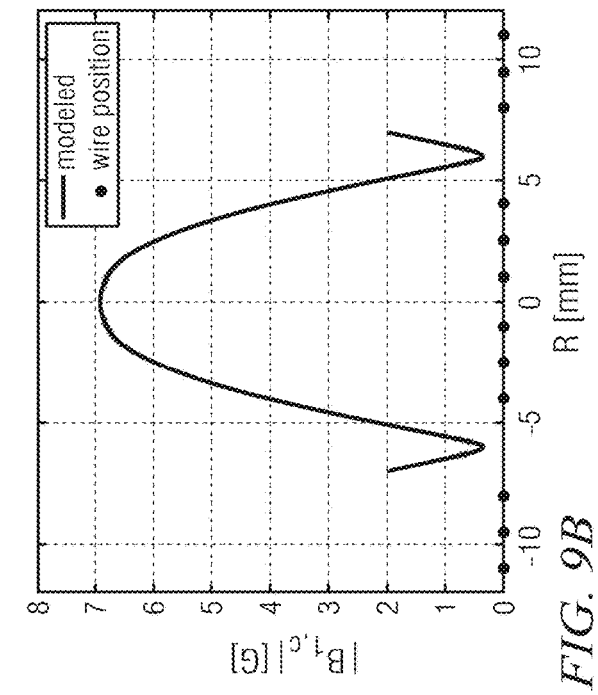

FIGS. 8A and 8B (collectively FIG. 8) depict plots of modelled and measured $B_0$ magnetic field generated by the particular magnet assembly described above with respect to FIG. 7A. FIG. 8A plots the magnetic field in units of Gauss versus distance along the axis of symmetry. Note that the $B_0$ magnetic field is approximately constant (unchanging with changing distance) over an axial distance ranging from about 2 to about 7 mm. FIG. 8B plots the magnetic field in units of Gauss versus distance along a lateral or radial direction perpendicular to the axis (at an axial distance of 6 mm). Note that the $B_0$ magnetic field is approximately constant (unchanging with changing distance) over a lateral (radial) distance ranging from about −5 to about 5 mm.

Figure 9A:
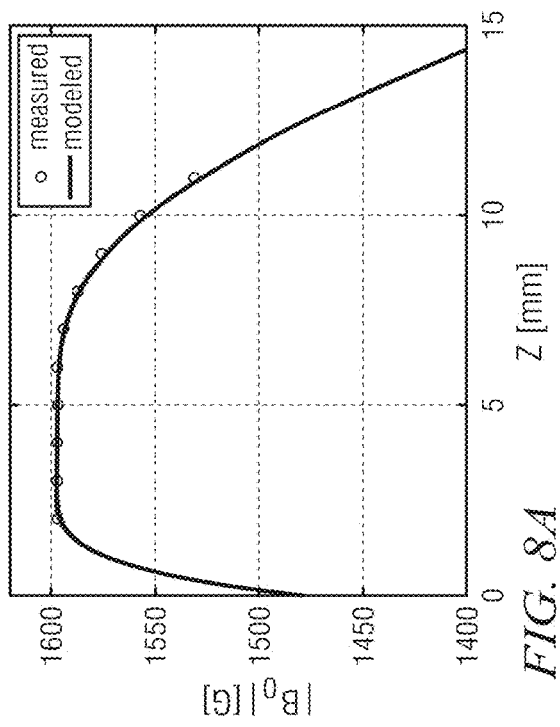
FIGS. 9A and 9B (collectively FIG. 9) depict plots of modelled and measured $B_1$ magnetic fields (measured in a direction perpendicular to the local $B_0$ field) generated by one example RF coil embodiment described with respect to FIG. 7B.
Figure 9B:
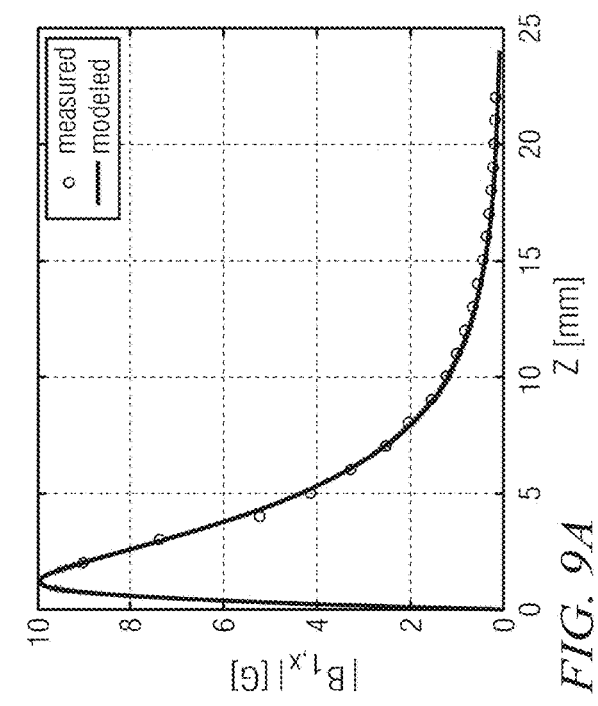

FIGS. 9A and 9B (collectively FIG. 9) depict plots of modelled and measured $B_1$ magnetic field (measured in a direction perpendicular to the local $B_0$ field) generated by the particular RF coil described above with respect to FIG. 7B. FIG. 9A plots the magnetic field in units of Gauss versus distance along the axis of symmetry. FIG. 9B plots the magnetic field in units of Gauss versus distance along a lateral or radial direction perpendicular to the axis (at an axial distance of 6 mm).

Figure 10A:
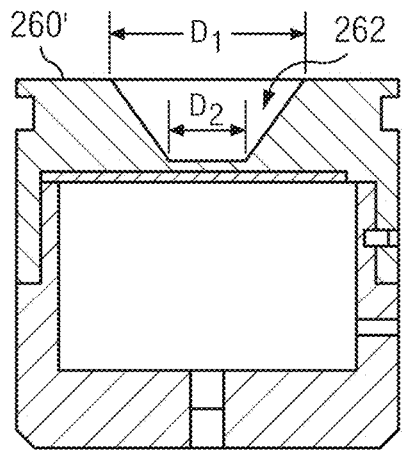
FIGS. 10A, 10B, and 10C (collectively FIG. 10) depict alternative nonmagnetic cap embodiments for use in the disclosed sensor embodiments.
Figure 10B:
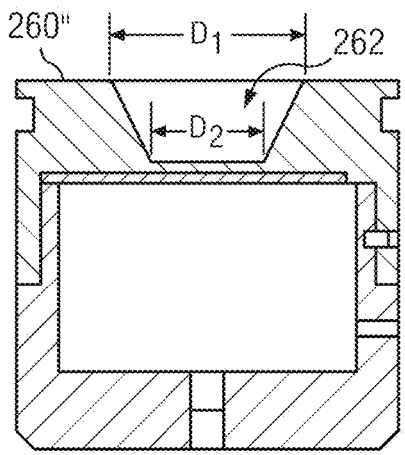
Figure 10C:
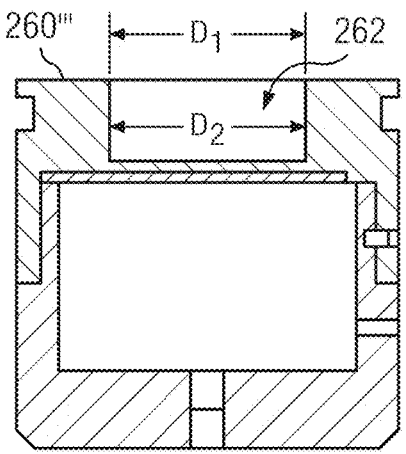

With continued reference to FIG. 6 and further reference to FIGS. 10A, 10B, and 10C (collectively FIG. 10), alternative nonmagnetic cap embodiments 260', 260'', and 260''' are depicted. As noted above, the fluid collector 262 may be advantageously shaped to accelerate (or exaggerate) the settling processes by concentrating solids at the bottom of the collector 262. It has been found that the fluid collector may advantageously be configured to have a cross sectional area or a lateral dimension (in a plane orthogonal to longitudinal axis 251) that increases with increasing axial distance to the coil 280 as depicted in FIGS. 10A and 10B. Moreover, cap embodiments having a larger ratio of lateral dimension D1 to lateral dimension D2 (as depicted in FIG. 10A) may accelerate the effects of fluid settling to a greater extent and may therefore be advantageous in certain operations. For example, the ratio of D1 to D2 may be greater than 1.5 (e.g., greater than 2, greater than 2.5, or even greater than 3). Notwithstanding the foregoing, the disclosed embodiments are not limited to having a fluid collector with a D1 to D2 ratio greater than 1. In certain embodiments (as depicted on FIG. 10C), the fluid collector may be shaped such that D1 equals (or is approximately equal to) D2.

Figure 11:
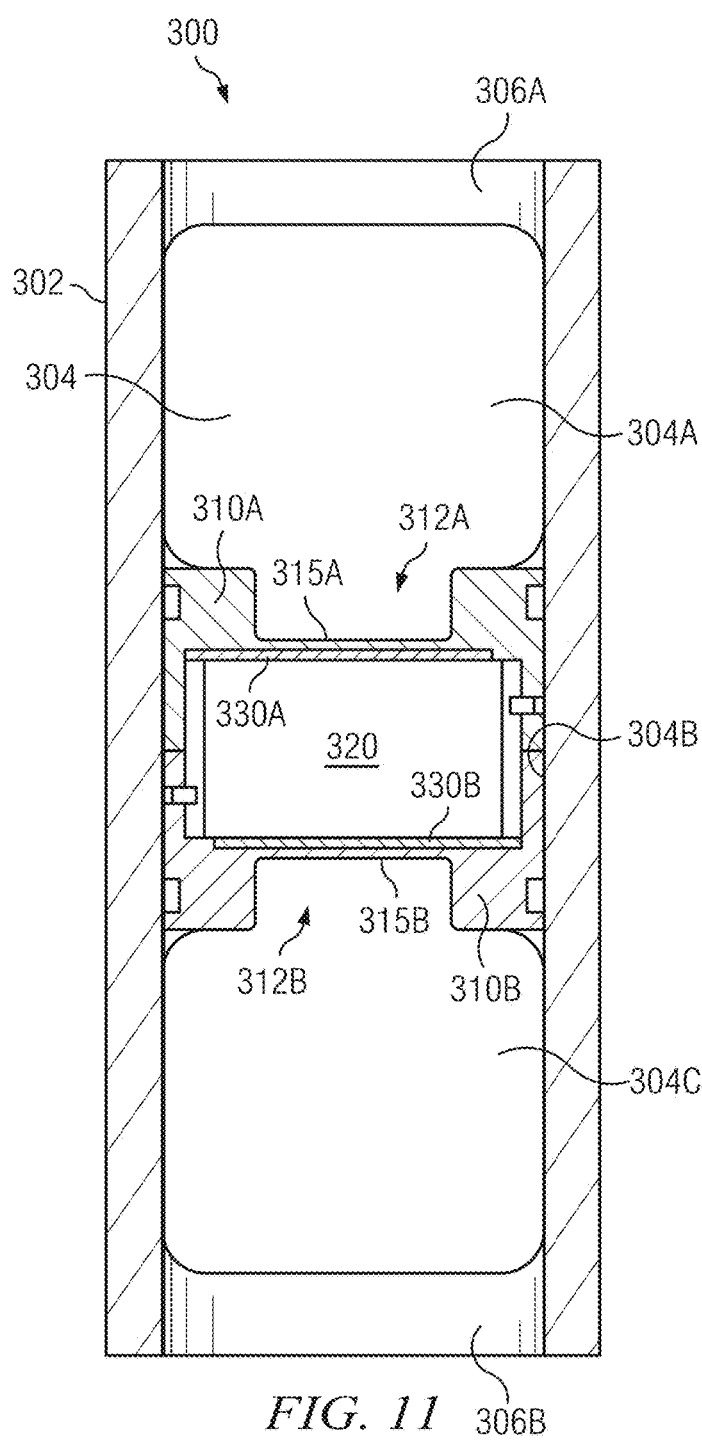
FIG. 11 depicts another sensor embodiment configured for use in making NMR measurements of aging and/or sagging of multi-phase fluids such as drilling fluids.

FIG. 11 depicts another sensor embodiment 300. Sensor 300 is configured for use in making NMR measurements of multi-phase fluids such as drilling fluids and may be used in surface system 80, for example as described above with respect to sensors 120 or 150, or in a laboratory NMR instrument. Sensor 300 includes a sensor housing 302 defining an inner chamber 304. In the depicted embodiment, the housing 302 includes first and second axially opposed open ends 306A and 306B providing for fluid communication between fluid in the chamber 304 and external to the housing 302. First and second nonmagnetic caps 310A and 310B are deployed in the chamber 304 and divide the chamber into first, second, and third regions 304A, 304B, and 304C. In the depicted embodiment, the caps are configured to sealingly engage an inner surface of the housing 302 (e.g., via O-rings) and isolate the second region 304B of the chamber from the first and third regions 304A and 304C.

As described above with respect to FIGS. 6 and 10, the caps 310A and 310B may be sized and shaped to define corresponding fluid collectors 312A and 312B in the first and third regions 304A and 304C. Although not depicted in FIG. 11, the fluid collectors 312A and/or 312B may be shaped to accelerate (or exaggerate) the effect of settling of components of the fluid thereby advantageously reducing the time required to study sagging of the fluid as also described above.

Sensor 300 further includes a magnet assembly 320 deployed in the second region (between the caps 310A and 310B). The magnet assembly is configured to generate static magnetic fields (the $B_0$ field) in each of the first and second fluid collectors (312A and 312B) (which are deployed on axially opposing sides of the assembly 320). First and second RF coils 330A and 330B are interposed between the magnet assembly 320 and the corresponding caps 310A and 310B. The RF coils 330A and 330B are configured to generate RF magnetic fields (the $B_1$ field) in the corresponding fluid collectors 312A and 312B. Further reference is made to FIGS. 7, 8, and 9 magnet assembly and RF coil embodiments and the corresponding generated $B_0$ and $B_1$ fields.

With continued reference to FIG. 11, it will be understood that double-sided sensor 300 is advantageously configured to include fluid collectors on both upwardly facing 315A and downwardly facing 315B surfaces of the sensor assembly. During operation, settling causes solids in the fluid to accumulate on or near surface 315A and to settle away from surface 315B such that NMR measurements can be made in the dense, settled region having a higher solids concentration and the less dense, oil-migration region having a lower solids concentration.

Figure 12:
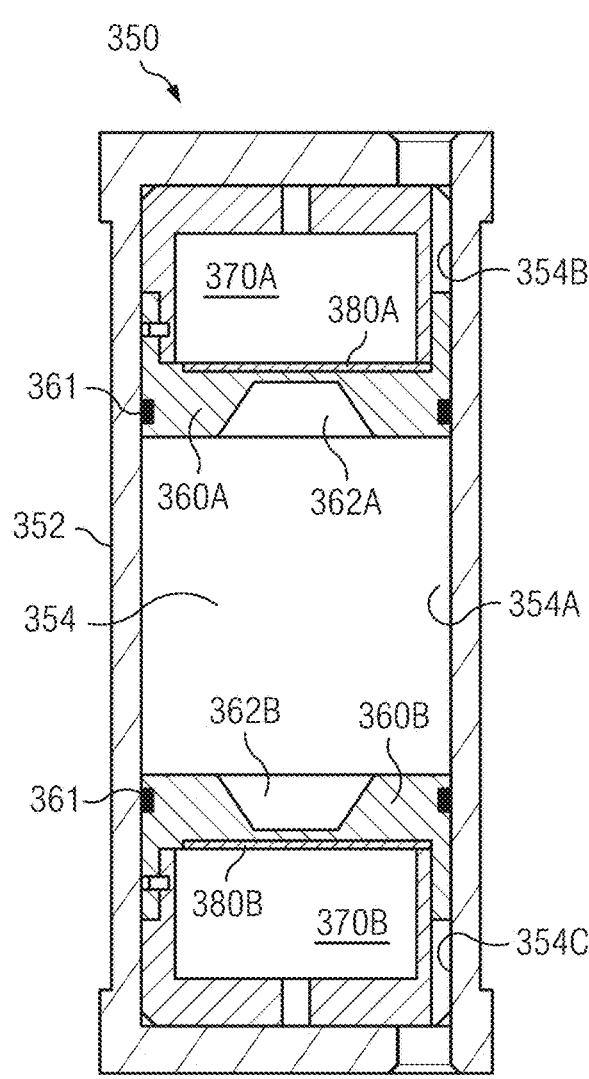
FIG. 12 depicts yet another sensor embodiment configured for use in making NMR measurements of aging and/or sagging of multi-phase fluids such as drilling fluids.

FIG. 12 depicts yet another sensor embodiment 350. Sensor 350 is configured for use in making NMR measurements of aging and/or sagging of multi-phase fluids such as drilling fluids in a laboratory NMR instrument. Sensor 350 includes a sensor housing 352 defining an inner chamber 354. First and second nonmagnetic caps 360A and 360B are deployed in the chamber 354 and divide the chamber into first, second, and third regions 354A, 354B, and 354C. In the depicted embodiment, the caps are configured to sealingly engage an inner surface of the housing 352 (e.g., via O-rings 361) and isolate the second and third regions 354B and 354C from the first region 354A. As described above with respect to FIGS. 6 and 10, the caps 360A and 360B may be sized and shaped to define corresponding fluid collectors 362A and 362B facing one another on opposing sides of the first region 354A.

Sensor 350 further includes first and second magnet assemblies 370A and 370B deployed in the second and third regions. The magnet assemblies are configured to generate static magnetic fields (the $B_0$ field) in each of the first and second fluid collectors (362A and 362B) as described in more detail above. First and second RF coils 380A and 380B are interposed between the magnet assemblies 370A and 370B and the corresponding caps 360A and 360B. The RF coils 380A and 380B are configured to generate RF magnetic fields (the $B_1$ field) in the corresponding fluid collectors 362A and 362B as described in more detail above. Further reference is made to FIGS. 7, 8, and 9 magnet assembly and RF coil embodiments and the corresponding generated $B_0$ and $B_1$ fields.

With continued reference to FIG. 12, it will be understood that sensor 350 may be utilized in a similar manner to sensor 300 (FIG. 11) and may enable NMR measurements to be made in upper and lower regions of a settling fluid.

Figure 13:
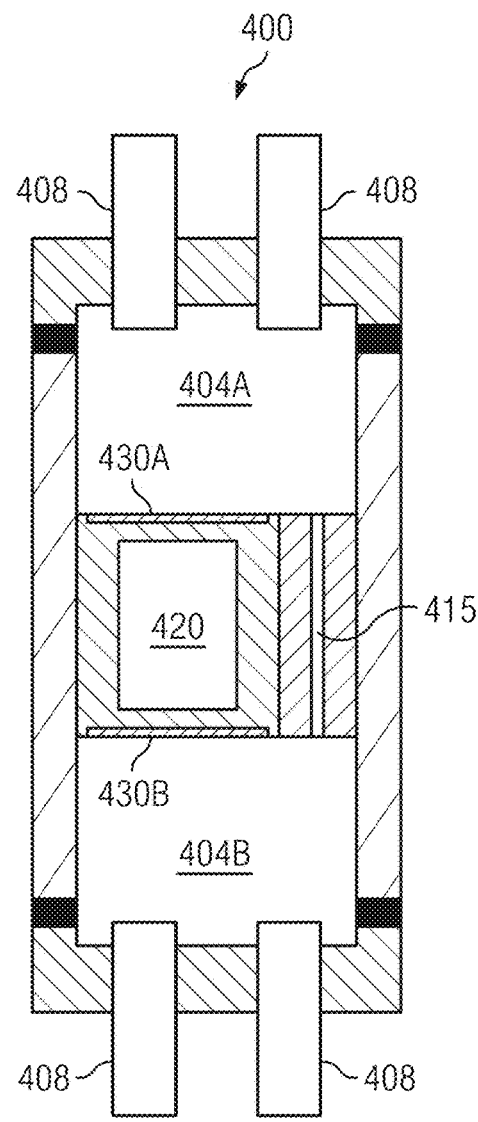
FIG. 13 depicts still another sensor embodiment configured for use in making NMR measurements of aging and/or sagging of multi-phase fluids such as drilling fluids.

FIG. 13 depicts still another sensor embodiment 400. Sensor 400 is similar to sensor 300 (FIG. 11) in that it is a double sided sensor in which a single magnet assembly 420 is configured to generate $B_0$ fields in fluid disposed in upper and lower chambers 404A and 404B located above and below the magnet assembly 420. The magnet assembly is deployed between first and second RF coils 430A and 430B which are in turn interposed between the assembly 420 and corresponding chambers 404A and 404B. Sensor 400 further includes valves 408 for charging the upper and lower chambers 404A and 404B with fluid.

Sensor 400 further includes one or more passageways 415 between the upper and lower chambers 404A and 404B. The passageways 415 are intended to facilitate the introduction of the fluid in the upper and lower chambers and ensure that no air bubbles are trapped prior closing valves 408. The passageway may be opened and closed, for example, via turning a screw(s) (not shown) threaded into the passageway(s). It will, of course, be understood that the disclosed embodiments are not limited to sensor embodiments including to any such passageway 415 or passageways.

Figure 14:
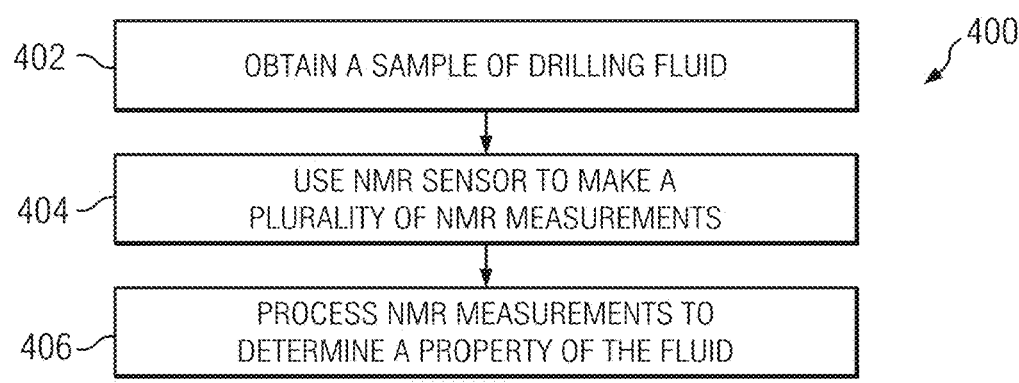
FIG. 14 depicts a flow chart of another disclosed method embodiment 400 for evaluating a sample of a multi-phase fluid such as a drilling fluid.

FIG. 14 depicts a flow chart of another disclosed method embodiment 400 for evaluating a sample of a multi-phase fluid such as drilling fluid. The method includes obtaining the sample of fluid at 402, for example, from a drilling rig or some other fluid source. The method further includes using a nuclear magnetic resonance (NMR) measurement sensor to make a plurality of an NMR measurements of the sample at a corresponding plurality of times at 404 while the sample ages. Example NMR sensors that may be used in method 400 are described above with respect to FIGS. 6-13. Such NMR sensors include a housing defining a chamber for receiving the fluid. A nonmagnetic cap is deployed in the chamber and divides the chamber into first and second regions. A magnet assembly is in the second region and is configured to generate a static magnetic field in the first region (i.e., in the fluid). An RF coil is interposed between the magnet assembly and the cap and is configured to generate an RF magnetic field in the first region.

The NMR measurements may be made, for example, as described above via applying a CPMG pulse sequence and measuring corresponding pulse echoes. The measurements may be made at any suitable times or substantially any suitable time interval (e.g., at 1 hour, 2 hour, 4 hour, 12 hour, or 1 day intervals) depending on the aging characteristics of the fluid. The disclosed embodiments are, of course, not limited in this regard.

The NMR measurements may be processed at 406 to determine at least one property of the fluid and/or to monitor changes in the fluid over the measurement time interval (i.e., over the plurality of times). The processing in 406 may include, for example, inverting each of the plurality of NMR measurements to obtain a corresponding plurality of T1T2 plots and evaluating the T1T2 plots to determine the property of the fluid and/or to monitor changes in the fluid with time. The fluid property may include substantially any fluid property, for example, including an NMR stability index, an oil to water ratio, a free oil fraction, a $T_1$ distribution, a $T_2$ distribution, and/or a diffusion coefficient.

The NMR stability index may be thought of as being a quantitative index indicative of a stability (or instability, e.g., via gel breakdown and collapse) of the obtained multi-phase fluid sample. In certain embodiments, the NMR stability index may quantify the overall evolution of the T1T2 plots with time, for example, to capture the full fluid dynamics of the sample with aging. For example, the cumulated difference between T1T2 plots may be computed over time. The index may then be used to compare various drilling fluids, for example, drilling fluids having the same chemical components but different concentrations of the components. In the aforementioned embodiments, the relative positions and amplitudes of peaks in the T1T2 plots may be indicative of the state of aging (or aged) fluid so that evaluating changes in the positions and amplitudes of may be used to quantify changes in the sample with time.

The NMR stability index may be configured such that an increasing index indicates increasing change between the T1T2 plots with aging. In such embodiments, an increasing NMR stability index is indicative of an increasing tendency of the fluid sample to sag (e.g., for certain components to coalesce or separate) with time. It will be understood that numerous mathematical constructs are applicable to quantify the similarity (or difference) between spectra or plots such as the T1T2 plots used herein. In certain advantageous embodiments, the NMR stability index quantifies changes to the T1T2 plots using a Bhattacharyya distance ($D_B$) computation, which is defined mathematically, for example, as follows:

$$D_B(sp_2, sp_1) = -\ln [\Sigma \sqrt{sp_1 * sp_2}]$$

where $sp_1$ and $sp_2$ represent first and second normalized T1T2 plots, * represents element-wise multiplication, and the summation is over the entire domain of the T1T2 plot. When the two T1T2 plots ($sp_1$ and $sp_2$) are identical then $D_B = 0$. Increasing differences between the two T1T2 plots are indicated by an increasing $D_B$.

In embodiments, in which the fluid sample is aged over multiple intervals (e.g., at 1 day intervals for three or more days), the NMR stability index may be configured to cumulate the evolution (or change) in the T1T2 plots over time. In one advantageous embodiment, the NMR stability index may be defined mathematically, for example, as follows:

$$SI_{NMR}(k) = \sum_{k=1}^{N} -\ln \left[ \sum \sqrt{sp_1 * sp_k} \right]$$

where $SI_{NMR}(k)$ represents the NMR stability index of the sample, N represents the number of sequential measurements over time with k=1, 2, ..., N representing individual ones of the N measurements, $sp_1 \ldots sp_k$ represent the normalized T1T2 plots, * represents element-wise multiplication, and the summation is over the entire domain of the T1T2 plot.

In certain optional embodiments it may be advantageous to obtain first and second samples. For example, a first sample including water based brine and second sample including deuterium oxide ($D_2O$) based brine may be obtained. In such embodiments the second sample may be essentially identical to the first sample with the exception of the brine composition (the $D_2O$ based brine replaces the water based brine). Further comparison of the T1T2 plots obtained from the first sample and the second sample may enable the contributions of oil based components and water based components in the drilling fluid to be separated (initially and/or as the sample ages). In general water based peaks are absent in the T1T2 plots for the sample including the $D_2O$ based brine thereby enabling peaks related to the oil-based components to be readily identified.

In embodiments employing $D_2O$ based brine, method 100 may further include computing first and second NMR stability indexes based on NMR measurements made while aging the drilling fluid including the water based brine and NMR measurements made while aging the drilling fluid including the $D_2O$ based brine. In such embodiments, the first stability index is indicative of the drilling fluid as a whole (including the oil based components, the water based components, and any solids). The second stability index is indicative of the stability of the drilling fluid absent the water based brine (i.e., including the oil based components and any solids). Such measurements enable the source of drilling fluid instability to be better identified, for example, to the water based brine, to the base oil, or to some interaction between these components. It may be advantageous in such embodiments to further compute a ratio or a difference of the first and second stability indexes to better characterize the fluid using a single parameter.

With further reference to FIG. 14, it will be understood that method 400 may be advantageously utilized to study fluid aging and make corresponding NMR measurements at temperatures and/or pressures above ambient temperatures and/or pressure. For example, measurements may be advantageously made at temperatures exceeding 100 degrees C. and/or pressures exceeding 100 psi.

Method 400 is now described in further detail by way of the following non-limiting example embodiments. The phase separation of a commercially available, multi-phase drilling fluid sample containing micronized barite and clay in an oil/brine mixture was evaluated at ambient conditions (room temperature and atmospheric pressure) (FIG. 15) and at non-ambient conditions (140 degrees C. and 200 psi in this example) (FIG. 16).

Figure 15A:
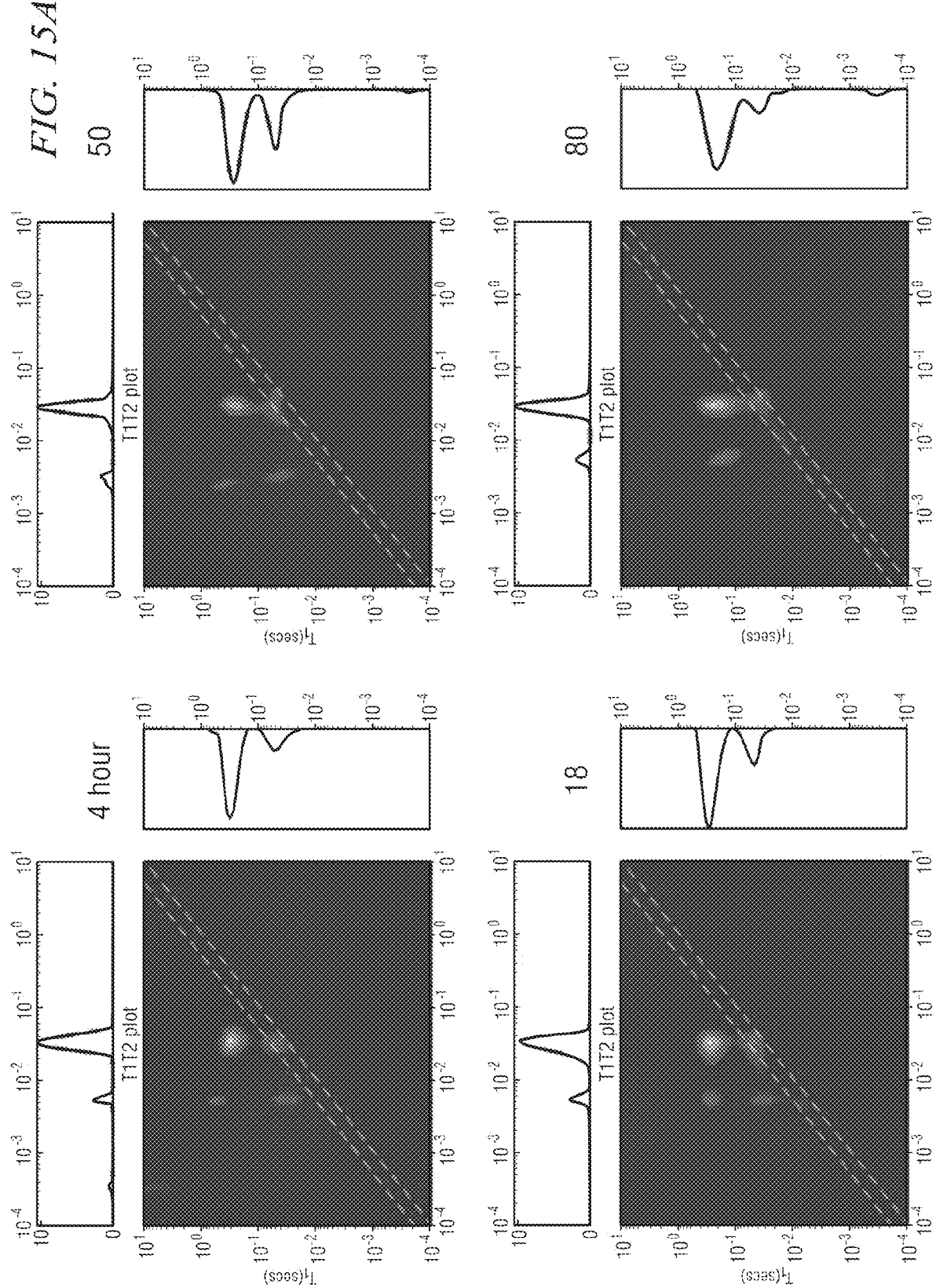
FIGS. 15A and 15B (collectively FIG. 15) depict example NMR data from an aging experiment conducted at ambient condition (room temperature and atmospheric pressure).
Figure 15B:
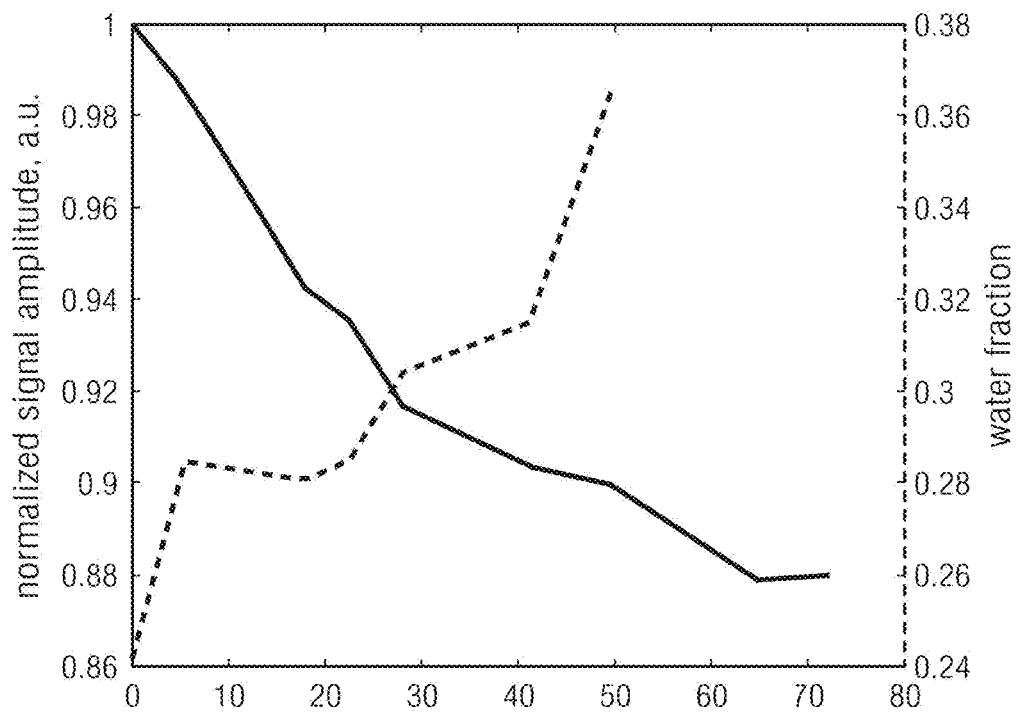

FIGS. 15A and 15B (collectively FIG. 15) depict example NMR data from an aging experiment conducted at ambient condition (room temperature and atmospheric pressure). FIG. 15A depicts T1T2 plots at times 4, 18, 50, and 80 hours of aging using the NMR sensor depicted in FIG. 6. The T1T2 plots show the effect of solid particle accumulation in the fluid collector of the nonmagnetic cap over the duration of the experiment as well as separation of the oil/brine emulsion. FIG. 15B depicts normalized CPMG echo (signal) amplitude (solid line) and computed water fraction of the fluid (dashed line) with respect to aging time. Note the monotonic decay in echo amplitude with time as the concentration of solids increases and the brine/water fraction increases with time in the fluid collector.

Figure 16B:
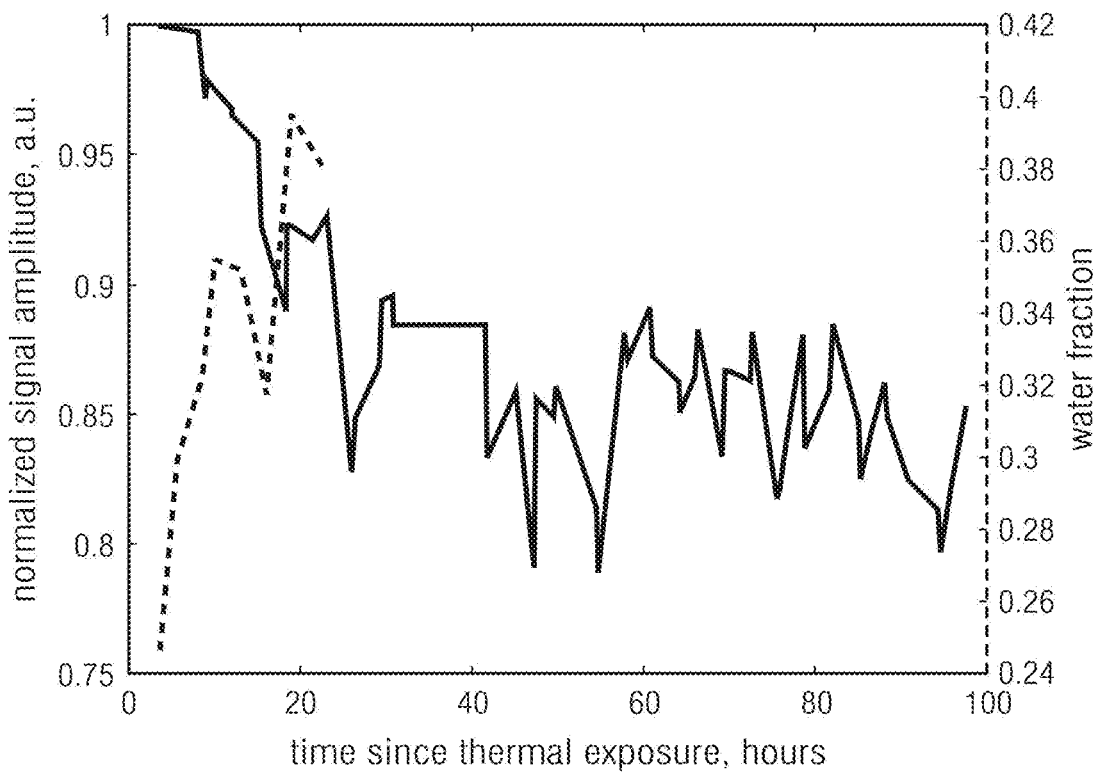
FIGS. 16A and 16B (collectively FIG. 16) depict example NMR data from an aging experiment conducted at non-ambient conditions (140 degrees C. and 200 psi in this example).
Figure 16A:
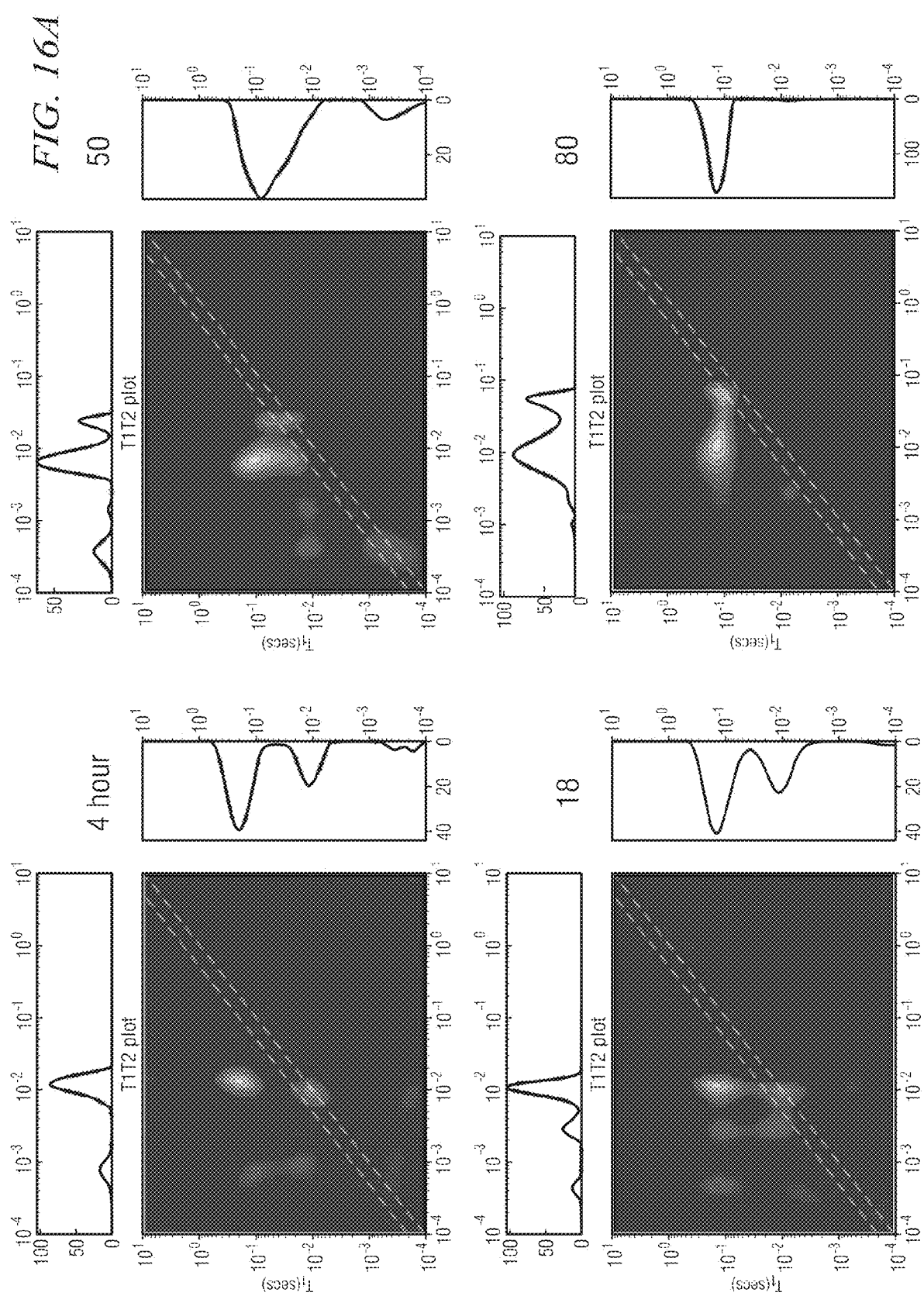

FIGS. 16A and 16B (collectively FIG. 16) depict example NMR data from an aging experiment conducted at non-ambient (140 degrees C. and 200 psi in this example). FIG. 16A depicts T1T2 plots at times 4, 18, 50, and 80 hours of aging using the NMR sensor depicted in FIG. 6. The T1T2 plots show the effect of solid particle accumulation in the fluid collector of the nonmagnetic cap over the duration of the experiment as well as separation of the oil/brine emulsion at high temperature conditions. FIG. 16B depicts normalized CPMG echo (signal) amplitude (solid line) and computed water fraction of the fluid (dashed line) with respect to aging time. Note the monotonic decay in echo amplitude with time as the concentration of solids increases and the brine/water fraction increases with time in the fluid collector.

With continued reference to FIGS. 15 and 16, it is evident that environmental conditionals (e.g., temperature and pressure) can strongly influence the settling/sagging process of a drilling fluid. For example, at ambient conditions (FIG. 15A) the oil and brine peaks remain well separated in T1 while the oil and brine peaks coalesce at higher (non-ambient) temperatures and pressures (FIG. 16A). Both room temperature and high temperature settling experiments clearly indicate solid buildup at the bottom of the fluid column, resulting in loss of signal amplitude with T1 providing robust oil/water contrast that is lost over time as settling progresses. High temperature conditions appear to accelerate the sagging in both the time to settle (blue curves) as well as increase the water fraction (red curves). Unique to the high temperature sagging, T2 appears to show contrast later in the settling process. Further investigation is required to understand the process.

It will be appreciated that the disclosed sensor and method embodiments are not limited to use with any particular type of drilling fluid. The disclosed sensor and method embodiments may be suitable for evaluating oil based and water based drilling fluids. Such fluids may include any number of solid weighting agents such as barite, manganese oxide, iron oxide, and/or calcium carbonate. The drilling fluids may further include substantially any suitable brine made up of various dissolved salts, for example, including sodium chloride, potassium chloride, calcium chloride, sodium bromide, potassium bromide, calcium bromide, zinc bromide, sodium formate, potassium formate, cesium formate, sodium acetate, potassium acetate, and the like, and mixtures thereof.

It will be further understood, that the disclosed sensor and method embodiments are not limited to use with drilling fluids but may be suitably used to evaluate substantially any multi-phase fluid or emulsion. For example, the disclosed embodiments may be used to evaluated settling of water based and/or oil based gravel packing fluids (that are commonly used in downhole completion operations and include fine sand and/or ceramic solids) or fracturing fluids (that include various solid components such as sand). The disclosed embodiments may also be utilized to monitor shelf life and/settling of substantially any slurry or colloidal suspension to evaluate settling or gelling of the sample with time.

Moreover the disclosed sensor and method embodiments are not limited to use in settling or sagging studies. For example, the disclosed sensor and method embodiments may be used to evaluate the precipitation and growth of various solid phase components in a fluid such as deposits (organic or inorganic) that may occur when solubility limits are exceeded or temperature and pressure conditions change with time. The disclosed sensor and method embodiments may be further utilized to evaluated dissolution of various solid phase components such as the salts and the aforementioned deposits.

It will be understood that the disclosure includes numerous embodiments. These embodiments include, but are not limited to, the following embodiments.

In a first embodiment, a nuclear magnetic resonance (NMR) sensor configured for making NMR measurements of a fluid, includes a housing defining a chamber; a non-magnetic cap deployed in the chamber and dividing the chamber into first and second regions, the cap sized and shaped to define a fluid collector in the first region; a magnet assembly deployed in the second region, the magnet assembly configured to generate a static magnetic field in the fluid collector; and a radio frequency (RF) coil interposed between the magnet assembly and the cap, the coil configured to generate an RF magnetic field in the fluid collector.

A second embodiment may include the first embodiment, wherein the housing has an open end for fluid entrance into the first region of the chamber; and the fluid collector faces and is in fluid communication with the open end.

A third embodiment may include any one of the first through second embodiments, wherein the cap sealingly engages an inner surface of the housing such that the second region is isolated from the first region.

A fourth embodiment may include any one of the first through third embodiments, wherein the magnet assembly and the RF coil are configured to define a zone of maximum NMR sensitivity in the fluid collector.

A fifth embodiment may include any one of the first through fourth embodiments, wherein the fluid collector is shaped such that a cross sectional area of a plane distal to the RF coil is greater than a cross sectional area of a plane proximate to the RF coil.

A sixth embodiment may include any one of the first through fifth embodiments, wherein the fluid collector is conical, pyramidal, a conical or pyramidal frustum in shape.

A seventh embodiment may include any one of the first through sixth embodiments, wherein the magnetic assembly includes a plurality of inner ring shaped permanent magnets deployed concentric with a corresponding plurality of outer ring shaped permanent magnets.

An eighth embodiment may include any one of the first through seventh embodiments, wherein: the housing includes first and second opposing open ends; the nonmagnetic cap includes first and second nonmagnetic caps deployed in the chamber and dividing the chamber into first, second, and third regions, the first and third regions being in fluid communication with the corresponding first and second open ends and a second region being disposed between the first and second caps, the first and second caps sized and shaped to define corresponding first and second fluid collectors facing the first and second open ends; the magnet assembly is configured to generate a static magnetic field in each of the first and second fluid collectors; and the RF coil includes a first RF coil interposed between the magnet assembly and the first cap and a second RF coil interposed between the magnet assembly and the second cap, the first and second RF coils configured to generate RF magnetic fields in the corresponding first and second fluid collectors.

A ninth embodiment may include any one of the first through eighth embodiments, wherein: the nonmagnetic cap includes first and second nonmagnetic caps deployed in the chamber and dividing the chamber into first, second, and third regions, the first region being interposed between the caps, each of the first and second caps sized and shaped to define corresponding first and second fluid collectors facing one another in the first region; the magnet assembly includes first and second magnet assemblies deployed in the corresponding second and third regions and configured to generate a static magnetic field in the corresponding first and second fluid collectors; and the RF coil includes a first coil interposed between the first magnet assembly and the first cap and a second RF coil interposed between the second magnet assembly and the second cap, the first and second RF coils configured to generate RF magnetic fields in the corresponding first and second fluid collectors.

In a tenth embodiment, a method for evaluating a fluid includes: (a) deploying at least one nuclear magnetic resonance (NMR) sensor in fluid communication with a multi-phase fluid at a surface location in a drilling rig, the NMR sensor including (i) a sensor housing defining a chamber, the chamber in fluid communication with the fluid, (ii) a magnet assembly deployed in the chamber and configured to generate a static magnetic field in at least a portion of the chamber, (iii) a radio frequency (RF) coil deployed in the chamber and configured to generate an RF magnetic field in at least the portion of the chamber, and (iv) a nonmagnetic cap deployed in the chamber and configured to provide a fluid tight seal between the fluid and the magnet assembly and the RF coil; (b) causing the NMR sensor to make a plurality of NMR measurements of the fluid at a corresponding plurality of times during operation of the drilling rig; and (c) processing the NMR measurements made in (b) to determine at least one property of the fluid and to monitor changes in the drilling fluid over the plurality of times.

An eleventh embodiment may include the tenth embodiment wherein: the multi-phase fluid is a drilling fluid; and the NMR sensor is deployed in at least one of a mud pit, a standpipe, and a return passageway on the drilling rig.

A twelfth embodiment may include any one of the tenth through eleventh embodiments wherein: the nonmagnetic cap is deployed in the chamber and divides the chamber into first and second regions, the first region in fluid communication with the drilling fluid, the cap sized and shaped to define a fluid collector in the first region; the magnet assembly is deployed in the second region and is configured to generate the static magnetic field in the fluid collector; and the RF coil is interposed between the magnet assembly and the cap and is configured to generate the RF magnetic field in the fluid collector.

A thirteenth embodiment may include any one of the tenth through twelfth embodiments wherein the magnet assembly and the RF coil are configured to define a zone of maximum NMR sensitivity in the fluid collector.

A fourteenth embodiment may include any one of the tenth through thirteenth embodiments wherein the fluid collector is shaped such that a cross sectional area of a plane distal to the RF coil is greater than a cross sectional area of a plane proximate to the RF coil.

A fifteenth embodiment may include any one of the tenth through fourteenth embodiments wherein the fluid collector is conical, pyramidal, or a conical or pyramidal frustum in shape.

A sixteenth embodiment may include any one of the tenth through fifteenth embodiments wherein the magnetic assembly includes a plurality of inner ring shaped permanent magnets deployed concentric with a corresponding plurality of outer ring shaped permanent magnets.

A seventeenth embodiment may include any one of the tenth through sixteenth embodiments wherein the processing in (c) comprises: (c1) inverting each of the plurality of NMR measurements to obtain a corresponding plurality of T1T2 plots; and (c2) evaluating the T1T2 plots to determine at least one property of the fluid and to monitor changes in the fluid over the plurality of times.

An eighteenth embodiment may include any one of the tenth through seventeenth embodiments wherein the at least one property comprises an NMR stability index or an oil water ratio, the NMR stability index being indicative of a stability of the fluid during aging.

A nineteenth embodiment may include the eighteenth embodiment wherein the NMR stability index comprises a Bhattacharyya distance ($D_B$) calculation.

In a twentieth embodiment, a method for evaluating a fluid includes: (a) obtaining a sample of a multi-phase fluid; (b) causing a nuclear magnetic resonance (NMR) measurement sensor to make a plurality of an NMR measurements of the sample at a corresponding plurality of times while the sample ages, the NMR sensor including (i) a housing defining a chamber, (ii) a nonmagnetic cap deployed in the chamber and dividing the chamber into first and second regions, the cap sized and shaped to define a fluid collector in the first region, (iii) a magnet assembly deployed in the second region, the magnet assembly configured to generate a static magnetic field in the fluid collector, and (iv) a radio frequency (RF) coil interposed between the magnet assembly and the cap, the coil configured to generate an RF magnetic field in the fluid collector; and (c) processing the NMR measurements made in (b) to determine at least one property of the fluid and to monitor changes in the fluid over the plurality of times.

A twenty-first embodiment may include the twentieth embodiment wherein (c) further comprises: (c1) inverting each of the plurality of NMR measurements to obtain a corresponding plurality of T1T2 plots; and (c2) processing the plurality of T1T2 plots in combination to determine the at least one property of the fluid and to monitor changes in the fluid over the plurality of times.

A twenty-second embodiment may include any one of the twentieth through twenty-first embodiments wherein the at least one property comprises an oil water ratio or an NMR stability index of the fluid which is indicative of a stability of the fluid during aging.

A twenty-third embodiment may include the twenty-second embodiment wherein the NMR stability index comprises a Bhattacharyya distance ($D_B$) calculation.

A twenty-fourth embodiment may include any one of the twenty second through the twenty-third embodiments wherein the NMR stability index is computed in (d) using the following mathematical equation:

$$SI_{NMR}(k) = \sum_{k=1}^{N} -\ln\left[\sum \sqrt{sp_1 * sp_k}\right]$$

wherein $SI_{NMR}$ (k) represents the NMR stability index of the sample of the fluid where k=1, 2, . . . , N sequential measurements over time, $sp_1$ and $sp_k$ represent the T1T2 plots obtained in (c), and * represents element-wise multiplication.

A twenty-fifth embodiment may include any one of the twentieth through the twenty-fourth embodiments wherein (c2) comprises evaluating changes in positions and amplitudes of corresponding peaks in the T1T2 plots to quantify changes in the sample with time.

A twenty-sixth embodiment may include any one of the twentieth through the twenty-fifth embodiments wherein (b) further comprises: aging the sample of the fluid at an elevated temperature greater than about 100 degrees C.; and making the plurality of NMR measurements at the elevated temperature; wherein the magnet assembly has a temperature about equal to the elevated temperature.

A twenty-seventh embodiment may include any one of the twentieth through the twenty-sixth embodiments wherein the sample is aged at a temperature greater than about 100 degrees C. and a pressure greater than about 100 psi.

A twenty-eighth embodiment may include any one of the twentieth through the twenty-seventh embodiments wherein: the fluid is a drilling fluid; the nonmagnetic cap is deployed in the chamber and divides the chamber into first and second regions, the first region in fluid communication with the drilling fluid, the cap sized and shaped to define a fluid collector in the first region; the magnet assembly is deployed in the second region and is configured to generate the static magnetic field in the fluid collector; and the RF coil is interposed between the magnet assembly and the cap and is configured to generate the RF magnetic field in the fluid collector.

A twenty-ninth embodiment may include any one of the twentieth through the twenty-eighth embodiments wherein the fluid collector is shaped such that a cross sectional area of a plane distal to the RF coil is greater than a cross sectional area of a plane proximate to the RF coil.

A thirtieth embodiment may include any one of the twentieth through the twenty-ninth embodiments wherein the fluid collector is conical, pyramidal, or a conical or pyramidal frustum in shape.

A thirty-first embodiment may include any one of the twentieth through the thirtieth embodiments wherein the magnetic assembly includes a plurality of inner ring shaped permanent magnets deployed concentric with a corresponding plurality of outer ring shaped permanent magnets.

Although an NMR sensor for monitoring fluid settling has been described in detail, it should be understood that various changes, substitutions and alternations can be made herein without departing from the spirit and scope of the disclosure as defined by the appended claims.

What is claimed is:

1. A nuclear magnetic resonance (NMR) sensor configured for making NMR measurements of a fluid, the sensor comprising:
a housing defining a chamber, wherein the housing includes first and second opposing open ends;
a nonmagnetic cap deployed in the chamber, the cap sized and shaped to define a fluid collector in the first region, wherein the nonmagnetic cap includes first and second nonmagnetic caps deployed in the chamber and dividing the chamber into first, second, and third regions, the first and third regions being in fluid communication with the corresponding first and second open ends and a second region being disposed between the first and second caps, the first and second caps sized and shaped to define corresponding first and second fluid collectors facing the first and second open ends;
a magnet assembly deployed in the second region, the magnet assembly configured to generate a static magnetic field in the fluid collector, wherein the magnet assembly is configured to generate a static magnetic field in each of the first and second fluid collectors; and
a radio frequency (RF) coil interposed between the magnet assembly and the cap, the coil configured to generate an RF magnetic field in the fluid collector, wherein the RF coil includes a first RF coil interposed between the magnet assembly and the first cap and a second RF coil interposed between the magnet assembly and the second cap, the first and second RF coils configured to generate RF magnetic fields in the corresponding first and second fluid collectors.

2. The NMR sensor of claim 1, wherein:
one of the first and second opposing open ends is for fluid entrance into the first region of the chamber; and
the fluid collector faces and is in fluid communication with one of the first and second opposing open ends.

3. The sensor of claim 1, wherein the magnet assembly and the RF coil are configured to define a zone of maximum NMR sensitivity in the fluid collector.

4. The sensor of claim 1, wherein one of the first or second fluid collectors is shaped such that a cross sectional area of a plane distal to the RF coil is greater than a cross sectional area of a plane proximate to the RF coil.

5. The sensor of claim 4, wherein one of the first or second fluid collectors is conical, pyramidal, a conical or pyramidal frustum in shape.

6. The sensor of claim 1, wherein the magnetic assembly includes a plurality of inner ring shaped permanent magnets deployed concentric with a corresponding plurality of outer ring shaped permanent magnets.

7. A nuclear magnetic resonance (NMR) sensor configured for making NMR measurements of a fluid, the sensor comprising:
a housing defining a chamber;
a nonmagnetic cap deployed in the chamber and dividing the chamber into first and second regions, the cap sized and shaped to define a fluid collector in the first region;

wherein the nonmagnetic cap includes first and second nonmagnetic caps deployed in the chamber and dividing the chamber into first, second, and third regions, the first region being interposed between the caps, each of the first and second caps sized and shaped to define corresponding first and second fluid collectors facing one another in the first region;

a magnet assembly deployed in the second region, the magnet assembly configured to generate a static magnetic field in the fluid collector; wherein the magnet assembly includes first and second magnet assemblies deployed in the corresponding second and third regions and configured to generate a static magnetic field in the corresponding first and second fluid collectors; and a radio frequency (RF) coil interposed between the magnet assembly and the cap, the coil configured to generate an RF magnetic field in the fluid collector, wherein the RF coil includes a first coil interposed between the first magnet assembly and the first cap and a second RF coil interposed between the second magnet assembly and the second cap, the first and second RF coils configured to generate RF magnetic fields in the corresponding first and second fluid collectors.

8. A method for evaluating a fluid, the method comprising:
(a) deploying at least one nuclear magnetic resonance (NMR) sensor in fluid communication with a multi-phase fluid at a surface location in a drilling rig, the NMR sensor including (i) a sensor housing defining a chamber, the chamber in fluid communication with the fluid, (ii) a magnet assembly deployed in the chamber and configured to generate a static magnetic field in at least a portion of the chamber, (iii) a radio frequency (RF) coil deployed in the chamber and configured to generate an RF magnetic field in at least the portion of the chamber, and (iv) a nonmagnetic cap deployed in the chamber and configured to provide a fluid tight seal between the fluid and the magnet assembly and the RF coil;
(b) causing the NMR sensor to make a plurality of NMR measurements of the fluid at a corresponding plurality of times during operation of the drilling rig; and
(c) processing the NMR measurements made in (b) to determine at least one property of the fluid and to monitor changes in the drilling fluid over the plurality of times.

9. The method of claim 8, wherein:
the multi-phase fluid is a drilling fluid; and
the NMR sensor is deployed in at least one of a mud pit, a standpipe, and a return passageway on the drilling rig.

10. The method of claim 8, wherein:
the nonmagnetic cap is deployed in the chamber and divides the chamber into first and second regions, the first region in fluid communication with the drilling fluid, the cap sized and shaped to define a fluid collector in the first region;
the magnet assembly is deployed in the second region and is configured to generate the static magnetic field in the fluid collector; and
the RF coil is interposed between the magnet assembly and the cap and is configured to generate the RF magnetic field in the fluid collector.

11. The sensor of claim 10, wherein the magnet assembly and the RF coil are configured to define a zone of maximum NMR sensitivity in the fluid collector.

12. The sensor of claim 10, wherein the fluid collector is shaped such that a cross sectional area of a plane distal to the RF coil is greater than a cross sectional area of a plane proximate to the RF coil.

13. The sensor of claim 12, wherein the fluid collector is conical, pyramidal, or a conical or pyramidal frustum in shape.

14. The sensor of claim 10 wherein the magnetic assembly includes a plurality of inner ring shaped permanent magnets deployed concentric with a corresponding plurality of outer ring shaped permanent magnets.

15. The method of claim 8, wherein the processing in (c) comprises:
(c1) inverting each of the plurality of NMR measurements to obtain a corresponding plurality of T1T2 plots; and
(c2) evaluating the T1T2 plots to determine at least one property of the fluid and to monitor changes in the fluid over the plurality of times.

16. The method of claim 15, wherein the at least one property comprises an NMR stability index or an oil water ratio, the NMR stability index being indicative of a stability of the fluid during aging.

17. The method of claim 16, wherein the NMR stability index comprises a Bhattacharyya distance ($D_B$) calculation.

18. A method for evaluating a fluid, the method comprising:
(a) obtaining a sample of a multi-phase fluid;
(b) causing a nuclear magnetic resonance (NMR) measurement sensor to make a plurality of an NMR measurements of the sample at a corresponding plurality of times while the sample ages, the NMR sensor including (i) a housing defining a chamber, (ii) a nonmagnetic cap deployed in the chamber and dividing the chamber into first and second regions, the cap sized and shaped to define a fluid collector in the first region, (iii) a magnet assembly deployed in the second region, the magnet assembly configured to generate a static magnetic field in the fluid collector, and (iv) a radio frequency (RF) coil interposed between the magnet assembly and the cap, the coil configured to generate an RF magnetic field in the fluid collector; and
(c) processing the NMR measurements made in (b) to determine at least one property of the fluid and to monitor changes in the fluid over the plurality of times.

19. The method of claim 18, wherein (c) further comprises:
(c1) inverting each of the plurality of NMR measurements to obtain a corresponding plurality of T1T2 plots; and
(c2) processing the plurality of T1T2 plots in combination to determine the at least one property of the fluid and to monitor changes in the fluid over the plurality of times.

20. The method of claim 19, wherein the at least one property comprises an oil water ratio or an NMR stability index of the fluid which is indicative of a stability of the fluid during aging.

21. The method of claim 20, wherein the NMR stability index comprises a Bhattacharyya distance ($D_B$) calculation.

22. The method of claim 20, wherein the NMR stability index is computed in (d) using the following mathematical equation:

$$SI_{NMR}(k) = \sum_{k=1}^{N} -\ln\left[\sum \sqrt{sp_1 * sp_k}\right]$$

wherein $SI_{NMR}(k)$ represents the NMR stability index of the sample of the fluid where k=1,2, ... , N sequential measurements over time, $sp_1$ and $sp_k$ represent the T1T2 plots obtained in (c), and * represents element-wise multiplication.

23. The method of claim 19, wherein (c2) comprises evaluating changes in positions and amplitudes of corresponding peaks in the T1T2 plots to quantify changes in the sample with time.

24. The method of claim 18, wherein (b) further comprises aging the sample of the fluid at an elevated temperature greater than about 100 degrees C.;
    making the plurality of NMR measurements at the elevated temperature; and
    wherein the magnet assembly has a temperature about equal to the elevated temperature.

25. The method of claim 24, wherein the sample is aged at a temperature greater than about 100 degrees C. and a pressure greater than about 100 psi.

26. The method of claim 18, wherein:
    the fluid is a drilling fluid;
    the nonmagnetic cap is deployed in the chamber and divides the chamber into first and second regions, the first region in fluid communication with the drilling fluid, the cap sized and shaped to define a fluid collector in the first region;
    the magnet assembly is deployed in the second region and is configured to generate the static magnetic field in the fluid collector; and
    the RF coil is interposed between the magnet assembly and the cap and is configured to generate the RF magnetic field in the fluid collector.

27. The sensor of claim 26, wherein the fluid collector is shaped such that a cross sectional area of a plane distal to the RF coil is greater than a cross sectional area of a plane proximate to the RF coil.

28. The sensor of claim 27, wherein the fluid collector is conical, pyramidal, or a conical or pyramidal frustum in shape.

29. The sensor of claim 26 wherein the magnetic assembly includes a plurality of inner ring shaped permanent magnets deployed concentric with a corresponding plurality of outer ring shaped permanent magnets.

* * * * *